US012648738B2

(12) United States Patent
Baumann et al.

(10) Patent No.: US 12,648,738 B2
(45) Date of Patent: Jun. 9, 2026

(54) METHOD FOR DETECTING A FAILURE OF AT LEAST ONE COMPONENT OF A CONTINUOUS ANALYTE MONITORING SYSTEM

(71) Applicant: Roche Diabetes Care, Inc., Indianapolis, IN (US)

(72) Inventors: Edgar Baumann, Mannheim (DE); Peter Kettenmann, Waghaeusel (DE); Frederic Wehowski, Hockenheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 556 days.

(21) Appl. No.: 18/183,353

(22) Filed: Mar. 14, 2023

(65) Prior Publication Data

US 2023/0233151 A1 Jul. 27, 2023

Related U.S. Application Data

(63) Continuation of application No. PCT/EP2021/075027, filed on Sep. 13, 2021.

(30) Foreign Application Priority Data

Sep. 15, 2020 (EP) .................................... 20196214

(51) Int. Cl.
*A61B 5/00* (2006.01)
*A61B 5/145* (2006.01)

(52) U.S. Cl.
CPC ........ *A61B 5/7221* (2013.01); *A61B 5/14546* (2013.01)

(58) Field of Classification Search
CPC .............. A61B 5/7221; A61B 5/14546; A61B 5/14532; A61B 5/1468; A61B 5/1486;
(Continued)

(56) References Cited

U.S. PATENT DOCUMENTS 5,954,685 A * 9/1999 Tierney ................ A61B 5/1486
604/20
6,175,752 B1 1/2001 Say et al.
(Continued)

FOREIGN PATENT DOCUMENTS

CN 102072982 A 5/2011
JP 2002-513602 A 5/2002
(Continued)

OTHER PUBLICATIONS

International Search Report and Written Opinion of the International Searching Authority, PCT/EP2021/075027, Oct. 11, 2021, 10 pages.

*Primary Examiner* — Tse W Chen
*Assistant Examiner* — Hy Khanh Doan
(74) *Attorney, Agent, or Firm* — Bose McKinney & Evans LLP

(57) ABSTRACT

A method for detecting a failure of at least one component of a continuous analyte monitoring system is disclosed. The continuous analyte monitoring system has a failure detection resistor and an analyte sensor having at least two measurement electrodes. A constant voltage is applied between the two measurement electrodes and a first response signal is measured. A failure detection signal that is distinguishable from the constant voltage and/or from the first response signal in frequency and/or in height is applied to the continuous monitoring system, and a second response signal to the failure detection signal is measured using the failure detection resistor. Information is determined depending on at least one actual property of the component by evaluating the first response signal and the second response signal. A failure is detected if the information deviates from an expected value by more than a predetermined tolerance.

11 Claims, 3 Drawing Sheets

(58) Field of Classification Search
CPC ... A61B 5/1495; A61B 5/7225; A61B 5/1451;
A61B 2562/0209
See application file for complete search history.

(56) References Cited

U.S. PATENT DOCUMENTS

| | | | |
|---|---|---|---|
| 8,594,760 | B2 | 11/2013 | Wieder et al. |
| 2008/0157743 | A1 | 7/2008 | Martin et al. |
| 2009/0164162 | A1 | 6/2009 | Sadayuki et al. |
| 2010/0169035 | A1 | 7/2010 | Liang et al. |
| 2015/0164382 | A1 | 6/2015 | Varsavsky et al. |
| 2017/0176566 | A1 | 6/2017 | Monreal et al. |
| 2020/0150073 | A1* | 5/2020 | Zafar .................. G01N 33/025 |
| 2020/0178868 | A1 | 6/2020 | Mueller et al. |
| 2020/0209179 | A1 | 7/2020 | Bohm et al. |

FOREIGN PATENT DOCUMENTS

| | | | |
|---|---|---|---|
| JP | 2018-047259 | A | 3/2018 |
| JP | 2019-500599 | A | 1/2019 |
| WO | WO 2017/153506 | A1 | 9/2017 |
| WO | WO 2021/180619 | A1 | 9/2021 |

* cited by examiner

152 — Apply V between two electrodes and measure response signal

154 — Apply failure detection signal and measure second response signal using failure detection resistor 156 — Determine information on component by evaluating first and second response signals; detect failure if information deviates from expected value 158 — Determine concentration of analyte

METHOD FOR DETECTING A FAILURE OF AT LEAST ONE COMPONENT OF A CONTINUOUS ANALYTE MONITORING SYSTEM

RELATED APPLICATIONS

This application is a continuation of International Patent Application No. PCT/EP2021/075027, filed Sep. 13, 2021, which claims priority to EP 20 196 214.9, filed Sep. 15, 2020, both of which are hereby incorporated herein by reference.

BACKGROUND

This disclosure teaches a method for detecting a failure of at least one component of a continuous analyte monitoring system, a method for determining a concentration of at least one analyte in body fluid using at least one continuous analyte monitoring system and a continuous analyte monitoring system. The continuous analyte monitoring system comprises at least one analyte sensor which may be or may comprise an electrochemical sensor configured for insertion into a body tissue of a user, specifically an insertable or implantable electrochemical sensor for monitoring of the at least one analyte in the body tissue and/or in a body fluid within the body tissue. The method and devices according to this disclosure may be used for detecting at least one analyte present in one or both of a body tissue or a body fluid, in particular the method and devices are applied in the field of detecting one or more analytes such as glucose, ketones, lactate, triglycerides, cholesterol or other analytes in body fluids such as blood or interstitial fluid or other body fluids, both in the field of professional diagnostics, in the field of hospital point of care, in the field of personal care and in the field of home monitoring. However, other fields of application are feasible.

In the field of medical technology and diagnostics, a large number of monitoring devices and methods for detecting at least one analyte in a body fluid are known. The method and monitoring devices may be used for detecting at least one analyte present in one or both of a body tissue or a body fluid, in particular one or more analytes, preferably metabolites such as glucose, lactate, ketones, triglycerides, cholesterol or other analytes in body fluids such as blood or interstitial fluid or other body fluids. Without restricting the scope of this disclosure, in the following, mainly reference is made to the determination of glucose by an electrochemical biosensor as an exemplary and preferred analyte.

A typical electrochemical biosensor comprises a biological recognition element, which can be an antibody, a DNA-string, a protein or more specifically an enzyme. These molecules specifically bind to or react with analyte molecules. The biological recognition element, here exemplary an enzyme, is in contact to a transducer, an element, which transforms the change in the biological recognition element into a measurable signal. A typical electrochemical biosensor uses a working electrode as a transducer. In the case of enzymatic electrodes, the charge (electrons) generated by the enzyme must be efficiently and/or quantitatively collected by the transducer. Depending on the used enzyme and the sensor construction, the charge transfer can be direct from the enzyme to the transducer, i.e., the working electrode, or redox mediated by, e.g., natural oxygen, redox-active polymers or other redox active substances. The here exemplary presented electrochemical sensor deploys the enzyme from the class of oxidoreductase, called glucose oxidase (GOx). GOx may use oxygen as an electron acceptor, reducing it to hydrogen peroxide. The latter is diffusing toward working electrode surface, which is polarized at a potential, sufficient for efficient oxidation of the hydrogen peroxide. Thus, the oxygen/hydrogen peroxide acts as redox mediator for electron transfer from the enzyme active center to the surface of the working electrode. Such scheme corresponds to an enzymatic biosensor of the first generation. In the second generation, other redox reagents are envisaged to replace oxygen. Such mediators may be either freely diffusing species, or bound in a polymer matrix or other way. Some examples of the redox active species are ferrocene and phenazine derivatives, quinones, ruthenium or osmium complexes.

Commonly used are electrochemical biosensors, which are based on a potentiometric measurement principle. Therefore, the electrochemical biosensor needs to be permanently polarized with a potential between a counter electrode and a working electrode. In this condition, a current that is proportional to the level of glucose present in the body fluid is flowing into the working electrode and outside of the counter electrode. The electronic device regulating the voltage and measuring the current is called "potentiostat." Typically, an analogue electronic is used to regulate voltage. This may be done using several operational amplifiers and at least one reference voltage.

There is a need to provide functional safety of the electrochemical biosensor and its components. Specifically, there is a need to provide means to detect if one component has a problem to avoid giving false analyte values. For example, if a value of a measurement resistor is changed due to short circuit, cracking in the component, aging or the like this could lead to errors on the measured analyte value. Usually, this detection is done by using analogue switches on both electrode contacts.

WO 2017/153506 A1 describes an analyte measuring patch for invasive measuring a concentration of an analyte, in particular glucose. The analyte measuring patch includes a sensor with a working electrode, a counter electrode and a reference electrode. The patch further includes an electronics unit with a microcontroller and a current measurement unit. The microcontroller includes a control output, a first analogue input and a second analogue input. The control output is operatively coupled with a control electrode, the control electrode being either of the working electrode or the counter electrode. The first analogue input is operatively coupled with a measurement electrode via the current measurement unit, the measurement electrode being either of the working electrode or the counter electrode. The second analogue input is operatively coupled with the reference electrode. The microcontroller is configured to control, by providing a control voltage to the control output, a potential difference between the working electrode and the counter electrode to equal a predefined polarization voltage.

U.S. Publication No. 2020/0209179 A1 described systems and methods for detecting damage to an analyte sensor using analyte sensor impedance values. A membrane integrity state of the analyte sensor may be based on an impedance parameter.

U.S. Publication No. 2020/178868 A1 discloses a method for detecting in vivo properties of a biosensor. In the method, a sensitivity-to-admittance relation is provided and a raw current in the biosensor is measured. An in-vivo current response is also measured at first and second operating points. A failsafe operation of the biosensor is monitored by using an in-vivo current response measured at the first and second operating points.

U.S. Publication No. 2010/169035 A1 describes methods and materials for observing the state of a sensor. A voltage, such as a voltage pulse is applied to the sensor in order to solicit a current response from which, for example, an impedance value can be derived. This impedance value can then be used as indicator for the sensor's state.

U.S. Pat. No. 8,594,760 B2 describes a measuring system for in vivo monitoring of an analyte concentration with malfunction detection which comprises an electrode system, a potentiostat and an evaluation unit. The electrode system has a working electrode, a reference electrode, and a counter electrode. The potentiostat is for adjusting a difference of potential between the electric potential of the working electrode and the electric potential of the reference electrode to a specified value and for measuring an electric current flowing between the working electrode and the counter electrode. The potentiostat comprises a working electrode terminal for connection to the working electrode, a reference electrode terminal for connection to the reference electrode, and a counter electrode terminal for connection to the counter electrode. The evaluation unit monitors the electric potential of the counter electrode and generates a malfunction signal when said potential is outside a specified reference range.

However, such known devices and methods are expensive and take valuable space on the board of the monitoring device. Specifically, analogue switches that have all the good characteristics for this application are expensive and take up valuable space on the board.

SUMMARY

This disclosure provides a method for detecting a failure of at least one component of a continuous analyte monitoring system, a method for determining a concentration of at least one analyte in body fluid using at least one continuous analyte monitoring system and a continuous analyte monitoring system, which at least partially avoid the shortcomings of known devices and methods of this kind and which at least partially address the above-mentioned challenges. Specifically, functional safety can be ensured with reduced costs and with very few additional components within an electronics unit of the continuous analyte monitoring system.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall also be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "failure detection resistor," "electrode," and "sensor," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding alternative embodiments of the invention, without any restrictions regarding the scope of the invention and without any restriction regarding the possibility of combining the features introduced in such way with other optional or non-optional features of the invention.

In a first aspect of this disclosure, a method for detecting a failure of at least one component of a continuous analyte monitoring system is disclosed.

The term "system" as used herein is a broad term and is to be given its ordinary and customary meaning to a person of ordinary skill in the art and is not to be limited to a special or customized meaning. The term specifically may refer, without limitation, to a group of at least two elements which may interact in order to fulfill at least one common function. The at least two components may be handled independently or may be coupled, connectable or integratable in order to form a common component. Thus, a system generally refers to a group of at least two elements or components which are capable of interacting in order to perform at least one common function, such as in order to perform at least one detection of at least one analyte in a body fluid and/or in order to contribute to a detection of the at least one analyte in the body fluid. The system generally may also be referred to as an assembly. The term "component" may refer to a subsystem, element or a constituent part of the system.

The term "monitoring" as used herein is a broad term and is to be given its ordinary and customary meaning to a person of ordinary skill in the art and is not to be limited to a special or customized meaning. The term specifically may refer, without limitation, to a process of continuously acquiring data and deriving desired information therefrom. Specifically, the monitoring may comprise detecting at least one analyte in the body fluid. The term "detecting" as used herein is a broad term and is to be given its ordinary and customary meaning to a person of ordinary skill in the art and is not to be limited to a special or customized meaning. The term specifically may refer, without limitation, to a process of establishing a presence and/or a quantity and/or a concentration of at least one analyte in the body fluid. Thus, the detection may be or may comprise a qualitative detection, i.e., simply determining the presence of the at least one analyte or the absence of the at least one analyte, and/or may be or may comprise a quantitative detection, which determines the quantity and/or the concentration of the at least one analyte. The monitoring of the analyte may comprise generating and evaluating a plurality of measurement signals, wherefrom the desired information is determined. Herein, the plurality of measurement signals may be recorded within fixed or variable time intervals or, alternatively or in addition, at an occurrence of at least one pre-specified event. In particular, the continuous analyte monitoring system may, especially, be adapted for the continuous monitoring of one or more analytes, in particular of glucose, such as for managing, monitoring and controlling a diabetes state.

The term "analyte monitoring system" as used herein is a broad term and is to be given its ordinary and customary meaning to a person of ordinary skill in the art and is not to be limited to a special or customized meaning. The term specifically may refer, without limitation, to an arbitrary system configured for monitoring at least one analyte in a body fluid of a user. The term "continuous analyte monitoring system" as used herein is a broad term and is to be given its ordinary and customary meaning to a person of ordinary skill in the art and is not to be limited to a special or customized meaning. The term specifically may refer, without limitation, to an analyte monitoring system configured for continuously monitoring the analyte in the body fluid of the user. The continuous analyte monitoring system or at least a part of the continuous analyte monitoring system may remain in the body tissue of the user for a predetermined period of time, such as for several hours, specifically for one or more days, more specifically for up to one week, even more specifically for up to two weeks or even more.

The term "analyte" as used herein is a broad term and is to be given its ordinary and customary meaning to a person of ordinary skill in the art and is not to be limited to a special or customized meaning. The term specifically may refer, without limitation, to an arbitrary element, component or compound which may be present in a body fluid and the concentration of which may be of interest for a user. Specifically, the analyte may be or may comprise an arbitrary chemical substance or chemical compound which may take part in the metabolism of the user, such as at least one metabolite. As an example, the at least one analyte may be selected from the group consisting of glucose, ketones, cholesterol, triglycerides, lactate. Additionally or alternatively, however, other types of analytes may be determined and/or any combination of analytes may be determined.

As further used herein, the term "body fluid" may, generally, refer to a fluid, in particular a liquid, which may typically be present in a body or a body tissue of the user and/or which may be produced by the body of the user. ("Body fluid" and "bodily fluid" can be used interchangeably.) Preferably, the body fluid may be selected from the group consisting of blood and interstitial fluid. However, additionally or alternatively, one or more other types of body fluids may be used, such as saliva, tear fluid, urine or other body fluids. During the detection of the at least one analyte, the body fluid may be present within the body or body tissue. Thus, the continuous analyte monitoring system may, specifically, be configured for detecting the at least one analyte within the body tissue.

As generally used within this disclosure, the term "user" may refer to a human being or an animal, independent from the fact that the human being or animal, respectively, may be in a healthy condition or may suffer from one or more diseases. As an example, the user may be a human being or an animal suffering from diabetes. However, additionally or alternatively, this disclosure may be applied to other types of users or patients or diseases.

The continuous analyte monitoring system comprises at least one analyte sensor. The term "sensor" as used herein is a broad term and is to be given its ordinary and customary meaning to a person of ordinary skill in the art and is not to be limited to a special or customized meaning. The term specifically may refer, without limitation, to an arbitrary element or device configured for detecting at least one condition or for measuring at least one measurement variable. The term "analyte sensor" as used herein is a broad term and is to be given its ordinary and customary meaning to a person of ordinary skill in the art and is not to be limited to a special or customized meaning. The term specifically may refer, without limitation, to a sensor configured for detecting quantitatively or qualitative at least one analyte. The analyte sensor may be or may comprise at least one electrochemical sensor. The term "electrochemical sensor" specifically may refer to a sensor based on electrochemical measurement principles, such as by using one or more of an amperometric, coulometric or a potentiometric measurement principle. Specifically, the electrochemical sensor may comprise at least one enzyme configured for performing at least one redox reaction in the presence of the analyte to be detected, wherein the redox reaction may be detected by electrical means. As used herein, the term "electrochemical detection" refers to a detection of an electrochemically detectable property of the analyte by electrochemical means, such as an electrochemical detection reaction. Thus, for example, the electrochemical detection reaction may be detected by comparing one or more electrode potentials, such as a potential of a working electrode with the potential of one or more further electrodes such as a counter electrode or a reference electrode. The detection may be analyte specific. The detection may be a qualitative and/or a quantitative detection.

The analyte sensor may be an in-vivo sensor. The term "in-vivo sensor" as used herein is a broad term and is to be given its ordinary and customary meaning to a person of ordinary skill in the art and is not to be limited to a special or customized meaning. The term specifically may refer, without limitation, to a sensor which is configured for being at least partially implanted into a body tissue of a user. The analyte sensor may be a subcutaneous analyte sensor. The analyte sensor may be configured for implantation into a body tissue of the user. More specifically the analyte sensor may be configured for continuous monitoring of the analyte. The analyte sensor may be fully implantable or partially implantable. The method according to this disclosure may be performed in vivo.

The analyte sensor comprises at least two measurement electrodes. The analyte sensor may be a two-electrode sensor comprising two measurement electrodes, in particular precisely two measurement electrodes, or a three-electrode sensor comprising three measurement electrodes, in particular precisely three measurement electrodes. The term "measurement electrode" as used herein is a broad term and is to be given its ordinary and customary meaning to a person of ordinary skill in the art and is not to be limited to a special or customized meaning. The term specifically may refer, without limitation, to an electrode which is or can be brought in contact with an electrolyte, in particular with a body fluid. The at least two measurement electrodes may be designed such that an electrochemical reaction may take place at one or more of the electrodes. Thus, the measurement electrodes may be embodied such that an oxidation reaction and/or reduction reaction may take place at one or more of the electrodes.

One of the measurement electrodes may be designed as working electrode. The term "working electrode" as used herein is a broad term and is to be given its ordinary and customary meaning to a person of ordinary skill in the art and is not to be limited to a special or customized meaning. The term specifically may refer, without limitation, to an electrode of the analyte sensor which is configured for measuring a signal, such as a voltage, a current, a charge or electrical/electrochemical potential, dependent on the degree of an electrochemical detection reaction taking place at the working electrode, for the purpose of detecting the at least one analyte. The working electrode may comprise at least one test chemical. The working electrode may fully or partially be covered with at least one test chemical, specifically at least one test chemical comprising at least one enzyme for detecting the at least one analyte. As an example, glucose oxidase (GOx) or glucose dehydrogenase (GDH) may be used. The test chemical, further, may comprise additional materials, such as binder materials, electrode particles, mediators or the like. Thus, as an example, the test chemical may comprise at least one enzyme, carbon particles, a polymer binder and $MnO_2$ particles. In another preferred embodiment, the test chemical may comprise an enzyme and a mediator polymer comprising a polymeric material and a metal containing complex, for example, a modified poly(vinylpyridine) backbone loaded with poly(bi-imidizyl) Os complexes covalently coupled through a bidentate linkage. Further, the at least one test chemical may be comprised in a single layer, or the test chemical may comprise a plurality of layers, such as one layer having the at least one enzyme and one or more additional layers having one or more additional functions, such as one or more diffusion barriers and/or one or more biocompatibility layers.

The other one of the measurement electrodes may be designed as counter electrode or auxiliary electrode. The term "counter electrode" as used herein is a broad term and is to be given its ordinary and customary meaning to a person of ordinary skill in the art and is not to be limited to a special or customized meaning. The term specifically may refer, without limitation, to an electrode adapted for performing at least one electrochemical counter reaction and/or configured for balancing a current flow due to the detection reaction at the working electrode. The counter electrode may be a part of the implanted or partially implanted analyte sensor, or may be an individual electrode, which is either implanted or partially implanted or placed somewhere else on the body, e.g., on the skin surface. In case of the analyte sensor comprises a two-electrode system comprising precisely two measurement electrodes, the counter electrode may complete the circuit such that charge can flow through an electrochemical cell, also denoted electrochemical system, given by the working electrode, the counter electrode and an electrolyte, such as the body fluid, and may maintain a constant counter electrode potential, also referred to as a constant reference potential, regardless of current. The working electrode may have a higher potential compared to the other one of the measurement electrodes, which is also denoted counter electrode.

Additionally, the analyte sensor may comprise at least one reference electrode. The term "reference electrode," also referred to as "pseudo reference electrode," specifically may refer, without limitation, to an electrode of the analyte sensor which is configured to provide an electrochemical reference potential which, at least widely, is independent of the presence or absence or concentration of the analyte. The reference electrode may be configured for being a reference for measuring and/or controlling a potential of the working electrode. The reference electrode may have a stable and well-known electrode potential. The electrode potential of the reference electrode may preferably be highly stable. One of the measurement electrodes may have several functionalities, as for instance, combined reference and counter electrode, also denoted combined counter-reference electrode, which has both, the function of the reference and counter electrodes, which means it provides a reference potential and balances the current flow from the working electrode.

The continuous analyte monitoring system comprises at least one component and at least one failure detection resistor. The component may be one or more of at least one measurement resistance configured for measurement of a sensor current of the continuous analyte monitoring system or at least one membrane element comprised by at least one of the measurement electrodes. The term "failure detection resistor" as used herein is a broad term and is to be given its ordinary and customary meaning to a person of ordinary skill in the art and is not to be limited to a special or customized meaning. The term specifically may refer, without limitation, to at least one resistor which can be used for failure detection. Specifically, the failure detection resistor may be an element of the continuous analyte monitoring system in addition to the component under failure detection. The failure detection resistor may have a known, such as predetermined or preknown, resistance value. The resistance value may be an average value determined, specifically pre-determined, from a plurality of reference measurements. The resistance value may be selected suitable for determining the failure of the respective component such as of the measurement resistance or the membrane element.

The term "failure" as used herein is a broad term and is to be given its ordinary and customary meaning to a person of ordinary skill in the art and is not to be limited to a special or customized meaning. The term specifically may refer, without limitation, to a deviation from a target value and/or a target behavior. The failure specifically may refer to a functional failure. The failure may occur due to short circuit, cracking in the component, aging or the like and may result in false or incorrect detection of the analyte.

The method comprises the method steps as given in the corresponding independent claim and as listed as follows. The method steps may be performed in the given order. Further, additional method steps may be present which are not listed. The method comprises the following steps:

i) applying a constant voltage between the at least two measurement electrodes of the analyte sensor and measuring a first response signal, ii) applying a failure detection signal distinguishable from the constant voltage and/or from the first response signal in frequency and/or in height to the continuous analyte monitoring system and measuring a second response signal to the failure detection signal using the failure detection resistor;

iii) determining an information depending on at least one actual property of the component by evaluating the first response signal and the second response signal, wherein a failure is detected if the information deviates from at least one expected value more than at least one predetermined tolerance.

The term "constant voltage" as used herein is a broad term and is to be given its ordinary and customary meaning to a person of ordinary skill in the art and is not to be limited to a special or customized meaning. The term specifically may refer, without limitation, to a constant potential difference or polarizing potential of arbitrary height in between the two measurement electrodes. The term "constant" may refer to a timely essentially unchanged height of the voltage, at least during failure detection procedure. The term "essentially unchanged height" may refer to unchanged height within tolerances, for example, of ±1% or even less, preferably of ±0.1% or less. The term "applying the constant voltage" as used herein is a broad term and is to be given its ordinary and customary meaning to a person of ordinary skill in the art and is not to be limited to a special or customized meaning. The term specifically may refer, without limitation, to polarizing the measurement electrodes. For example, the counter electrode may be grounded and the constant voltage may be applied to the working electrode. For example, the constant voltage may be about 50 mV. Other values of constant voltage may be possible. The constant voltage may depend on chemistry at the measurement electrodes. Selecting suitable constant voltage depending on the chemistry at the measurement electrodes is known to the person skilled in the art.

The term "response signal" as used herein is a broad term and is to be given its ordinary and customary meaning to a person of ordinary skill in the art and is not to be limited to a special or customized meaning. The term specifically may refer, without limitation, to a measurable signal generated in response to application of voltage or current of the continuous analyte monitoring system. The term "first response signal" as used herein is a broad term and is to be given its ordinary and customary meaning to a person of ordinary skill in the art and is not to be limited to a special or customized meaning. The term specifically may refer, without limitation, to at least one current signal or at least one voltage signal generated by the analyte sensor in a situation of a constant voltage between the at least two measurement electrodes.

The analyte sensor may comprise and/or may be connected to at least one measuring device and/or may be part of at least one measuring device, in particular at least one potentiostat or galvanostat, configured for detecting the at least one analyte. Operating principles of potentiostats and galvanostats are generally known to the person skilled in the art. The potentiostat may be configured for generating and/or applying the constant voltage. By applying a constant voltage, a constant potential difference between the measurement electrodes may be achieved. The constant potential difference may also be referred to as polarization voltage of the analyte sensor. In situation of a constant potential difference between the measurement electrodes a current that is proportional to the level of glucose present into the body of the user may be flowing into the working electrode and outside of the counter electrode. The constant voltage may be a continuous direct current (DC) signal which polarizes an electrochemical cell of the analyte sensor, and serves as the "motor" for the amperometric measurement of the analyte oxidized by GOx. The constant voltage may be adjusted from time to time or continuously in order to give the analyte sensor its polarization voltage, preferably, in order to keep the predefined polarization voltage at the analyte sensor.

In particular, the potentiostat may be configured for monitoring and maintaining a potential applied at the working electrode. The potentiostat may be configured for monitoring and maintaining the potential between the reference electrode and the working electrode. As outlined above, one of the measurement electrodes may have several functionalities and may be designed as combined counter-reference electrodes. The potentiostat may be configured for monitoring and maintaining the potential between the combined counter-reference electrode and the working electrode. The potentiostat may be configured for maintaining the desired polarization voltage, for example, 50 mV, between the reference electrode and the working electrode or between the working electrode and the combined counter-reference electrode. The current flowing between working and counter or combined counter-reference electrode may be measured at the working or counter or combined counter-reference electrode. The reference electrode may be used to monitor the potential of the working electrode.

The continuous analyte monitoring system may comprise at least one controlling unit, in particular a digital controlling unit such as at least one microcontroller unit (MCU). The MCU may be configured for regulating the voltage between the measurement electrodes. The analyte sensor may comprise the MCU and/or may be directly connectable to the MCU. For example, the analyte sensor may comprise sensor contacts via which the analyte sensor, in particular the measurement electrodes can be connected to the MCU. Usage of an MCU has several advantages. Specifically, only very few analogue components are required. Moreover, there is no need for any voltage regulator or additional voltage reference. The MCU may comprise a Digital to Analog converter (DAC) or at least one Pulse Width Modulator (PWM) which is configured for applying the constant voltage to the measurement electrodes, in particular to the working electrode. The MCU may comprise a plurality of Analog to Digital converter (ADC) channels. The MCU may comprise at least one ADC channel for determining voltage output at the counter electrode. The potential at the counter electrode may be measured and therefore known from the MCU. The MCU is configured for measuring the potential at the counter electrode via the ADC channel and to adjust the DAC or PWM in order to get the pre-defined polarization of the measurement electrodes.

As will be outlined in more detail below, the continuous analyte monitoring system may comprise at least one measurement resistance used for measuring the current flowing outside of the counter electrode. The continuous analyte monitoring system may comprise at least one first measurement resistance which may be configured for converting the current flowing out of the counter electrode into a voltage proportional to the current. The MCU may further comprise at least one amplifier such as an operational amplifier. Additionally or alternatively, the amplifier may be an external amplifier which may be connected to the MCU. The amplifier may be configured for amplifying the voltage, such as by a constant gain factor, before measurement at the ADC channel. The MCU may further comprise at least one output which, for detection of the analyte, may be put at ground, i.e., logical 0. The continuous analyte monitoring system may comprise at least one second measurement resistance in parallel to the first measurement resistance and connected to the output in case of being at logical 0. The second measurement resistance may have a resistance much higher than the first measurement resistance. Thus, the current from the counter electrode may be flowing into both the first measurement resistance and the second measurement resistance. If those two measurement resistances would have known and unchanged values, it would be possible to calculate the current flowing out of the counter electrode using the ADC channel by using Ohm's law.

The term "failure detection signal" as used herein is a broad term and is to be given its ordinary and customary meaning to a person of ordinary skill in the art and is not to be limited to a special or customized meaning. The term specifically may refer, without limitation, to a current or voltage signal distinguishable from the constant voltage and/or from the first response signal in at least one property which can be used for detecting the failure of the component. The failure detection signal is distinguishable from the constant voltage and/or from the first response signal in frequency and/or in height. For example, the failure detection signal may be significantly smaller than the constant voltage and/or the first response signal. For example, the failure detection signal may be significantly shorter such as a pulse than the constant voltage.

The term "second response signal" as used herein is a broad term and is to be given its ordinary and customary meaning to a person of ordinary skill in the art and is not to be limited to a special or customized meaning. The term specifically may refer, without limitation, to at least one current signal or at least one voltage signal determined using the failure detection resistor in response to application to the failure detection signal. Specifically, the second response signal may be measurable by using the failure detection resistor.

The term "property of the component" as used herein is a broad term and is to be given its ordinary and customary meaning to a person of ordinary skill in the art and is not to be limited to a special or customized meaning. The term specifically may refer, without limitation, to at least one arbitrary property of the component influencing the analyte detection. For example, the component may be a measurement resistance and the property may be a resistance value. For example, the component may be a membrane element comprised by at least one of the measurement electrodes and the property may be at least one membrane property. The term "actual property" as used herein is a broad term and is to be given its ordinary and customary meaning to a person of ordinary skill in the art and is not to be limited to a special or customized meaning. The term specifically may refer, without limitation, to a current property of the component, which may depend on a status or a condition of the component. The status or condition of the component may change during time such as due to aging, mechanical influences, temperature influences and the like. The information depending on the actual property may be an arbitrary information indicating status or condition of the component. The term "expected value" as used herein is a broad term and is to be given its ordinary and customary meaning to a person of ordinary skill in the art and is not to be limited to a special or customized meaning. The term specifically may refer, without limitation, to a target value of the component.

The term "evaluating" as used herein is a broad term and is to be given its ordinary and customary meaning to a person of ordinary skill in the art and is not to be limited to a special or customized meaning. The term specifically may refer, without limitation, to deriving the at least one representative result from the respective response signal.

Step iii), in particular, may comprise comparing the information depending on the actual property and the expected value. A failure is detected if the information deviates from at least one expected value more than at least one predetermined tolerance. For example, a failure may be detected if the information deviates from at least one expected value more than $\pm 10\%$, preferably $\pm 5\%$, more preferably $\pm 2\%$.

For example, the component may be at least one of the measurement resistances of the continuous analyte monitoring system. The term "measurement resistance" as used herein is a broad term and is to be given its ordinary and customary meaning to a person of ordinary skill in the art and is not to be limited to a special or customized meaning. The term specifically may refer, without limitation, to a resistor which can be used for determining the current flowing out of the counter electrode. The measurement resistance can be used for measurement of a sensor current of the continuous analyte monitoring system. As outlined above, the continuous analyte monitoring system may comprise a measurement resistance which may be connected to the counter electrode and which may be configured for converting the current flowing out of the counter electrode into a voltage proportional to the current. As outlined above, the MCU may further comprise the at least one output which, for detection of the analyte, may be put at ground, i.e., logical 0. The continuous analyte monitoring system may comprise the at least one second measurement resistance in parallel to the first measurement resistance and connected to the output in case of being at logical 0. The second measurement resistance may have a resistance much higher than the first measurement resistance. Thus, the current flowing outside of the counter electrode may be flowing into the first and second measurement resistances. The voltage proportional to the current flowing out of the counter electrode may be measured, such as via the at last one ADC channel of the MCU. If the value of the first measurement resistance and the second measurement resistance would be known and unchanged, it would be possible to determine the current flowing into the first measurement resistance from the measured voltage using Ohm's law.

The method may comprise determining if the measurement resistances are correctly working. Specifically, the method may comprise determining if a measuring chain of the continuous analyte monitoring system is correctly working. The measuring chain may comprise the measurement resistances and further elements such as the at least one amplifier. If one of the elements of the measuring chain is not correctly working this may result in erroneous measurement results of the analyte concentration. The method may comprise detecting if there is a failure in at least one of the measurement resistances. The failure may be a failure of the first measurement resistance and/or of the second measurement resistance. For example, failure in at least one of the measurement resistances may be detected using the second measurement resistance. Thus, the second measurement resistance may be used as failure detection resistor.

Step i) may comprise applying the constant voltage between the measurement electrodes and determining a first current $I_1$ as first response signal using the measurement resistance. Step ii) may comprise applying a second current $I_2$ as failure detection signal to the continuous analyte monitoring system and measuring a resulting total current $I_{tot}$ as second response signal using the failure detection resistor. The second measurement resistance may be a resistor arranged in parallel to the first measurement resistance. The resistance value of the failure detection resistor may be higher than the resistance value of the first measurement resistance. For example, the resistance value of the failure detection resistor may be around 100 times higher. A small additional current may injected into the first measurement resistance by using the failure detection resistance. As outlined above, for detecting the at least one analyte, the output normally may be put at ground, i.e., logical 0. For detecting the failure, a logical 1 may be put on the output which results in adding a small current flowing over the failure detection resistor into the first measurement resistance. This current may be dependent on the current already flowing from the analyte sensor and on the values of the failure detection resistor and the first measurement resistance. The second current $I_2$ may be significantly smaller than the first current $I_1$. For example, the second current $I_2$ may be around 5 nA or less, such as 3 nA.

In step iii) a failure may be detected if the resulting total current $I_{tot}$ deviates more than the predetermined tolerance from a sum of the first current $I_1$ and the second current $I_2$. For example, the predetermined tolerance may be ±5%, preferably ±2%. Specifically, as all values, the current values $I_1$, $I_2$ and $I_{tot}$ and the target value of the first measurement resistance and of the failure detection resistor, are known it is possible to check if there is a failure. Thus, by first measuring before application of the additional current and in response to the additional current, it is possible to check if the measurement resistances are working correctly. The proposed technique allows for testing the whole I to U converter, including the amplifier, and the resistors around it.

For example, the component may be the membrane element comprised by at least one of the measurement electrodes. For example, the membrane element may be applied to the working electrode. The term "membrane element" as used herein is a broad term and is to be given its ordinary and customary meaning to a person of ordinary skill in the art and is not to be limited to a special or customized meaning. (The term "membrane" is used interchangeably herein with "membrane element.") The term specifically may refer, without limitation, to at least one element configured for controlling and/or limiting diffusion of the analyte to the electrode to which the membrane element is applied. Thus, the membrane element may be configured as diffusion limiting membrane. However, the membrane element may have even more functionalities, such as providing biocompatibility. The membrane element may have further functions such as blocking of leakage of components below the membrane element such as of the enzyme or other components comprised in any one of the at least two measurement electrodes. The membrane element may also be configured as a blocking membrane. As used herein, the term "blocking" may refer to preventing leakage of inner components of a sensitive layer of the working electrode but not to the analyte. The membrane element may be configured for maintaining of sensor integrity, by for instance keeping the enzyme or redox mediator from leaching, thus gradation of the whole sensor. Independently on the role of the membrane element, its altering may be compensated.

The membrane element may comprise at least one polymer. The membrane element may be applied to the working electrode as thin polymer film. For example, the membrane element may be or may comprise Poly-(4-(N-(3-sulfonatopropyl) pyridinium)-co-(4vinyl-pyridine)-co-styrene (5%/90%/5%) or hydrophilic Polyurethane such as HP60D20 available from Lubrizol®. For example, the membrane element may comprise at least one of the following polymer classes and/or their copolymer: Poly(4 vinyl pyridine), Polymethacrylate, Polyacrylate, Polyvinyl pyrrolidone, Polyvinyl alcohol (PVA), Polyethylene glycol.

The membrane element may have at least one membrane property which may depend on different parameters such as temperature, composition of interstitial fluid, thickness of the membrane element, aging, swelling degree, mechanical stresses and the like. Changes in membrane property may result in erroneous measurement results. The term "membrane property" as used herein is a broad term and is to be given its ordinary and customary meaning to a person of ordinary skill in the art and is not to be limited to a special or customized meaning. The term specifically may refer, without limitation, to an arbitrary physical property of the membrane element influencing the determining of the analyte. Specifically, the membrane property may be permeability of the membrane element. The term "permeability" as used herein is a broad term and is to be given its ordinary and customary meaning to a person of ordinary skill in the art and is not to be limited to a special or customized meaning. The term specifically may refer, without limitation, to a material parameter characterizing transmission properties of the membrane element, specifically passing of substances through the membrane element. Further specifically, permeability may refer to permeability for a specific analyte since molecules and ions of the analytes may have different sizes, shapes and charge. In an embodiment, the permeability refers to the permeability of the membrane for glucose. Permeability of the membrane element can be measurable by determining an electrical resistance of the membrane element, denoted as membrane resistance. Permeability of the membrane element for a specific analyte $p_{Analyt}$ may be determined by $p_{Analyt}=f^*p$, wherein p is the permeability determined via the electrical resistance of the membrane element and f is a conversion factor. The conversion factor may be determined in calibration experiments using known glucose values.

Permeability of the membrane element for certain compounds may be proportional to the membrane's swelling degree. The swelling degree may correspond to the degree of water uptake. The swelling degree of the membrane may depend on its hydrophilicity. The membrane's swelling degree may directly affect the amount and/or mobility and, thus, the permeability of the membrane for certain compounds. The conductivity of an electrolyte like water or body fluid, such as interstitial fluid is directly linked to so-called total dissolved solids whereby ions, such as H+, OH−, Na+, K+, Cl− and other have the most contribution. Therefore, also the conductivity of the membrane which has taken up water or body fluid such as interstitial fluid also is directly linked to the total dissolved solids. The more charge carriers are present and the more mobile they are, the lower is the measured electrical resistance, by otherwise constant conditions, such as, e.g., cell geometry. Thus, the electrical resistance, or reversely, electric conductivity of the membrane element may depend on quantity and mobility of ions present in the membrane.

The continuous analyte monitoring system may comprises at least two serial failure detection resistors $R_3$, $R_4$ in series with the membrane resistance. Each of the two serial failure detection resistors may have a known and/or predetermined resistance value. Step i) may comprise measuring a base voltage as a first response signal of the continuous analyte monitoring system. The base voltage may be a polarization voltage of the analyte sensor due to the application of the constant voltage. Specifically, the base voltage corresponds to the constant voltage.

Step ii) may comprise generating at least one fast-transient voltage signal and applying the fast-transient voltage signal as a failure detection signal to the measurement electrodes. The term "fast-transient voltage" as used herein is a broad term and is to be given its ordinary and customary meaning to a person of ordinary skill in the art and is not to be limited to a special or customized meaning. The term specifically may refer, without limitation, to at least one arbitrary voltage change in between the two measurement electrodes. The arbitrary voltage change may have fast transient signal flanks, in particular two very steep edges The fast-transient voltage may comprise a square wave form and/or a sine wave form. The fast-transient voltage may comprise a non-continuous signal such as a pulse. Specifically, the fast-transient voltage may comprise a fast transition square wave.

The term "pulse" as used herein is a broad term and is to be given its ordinary and customary meaning to a person of ordinary skill in the art and is not to be limited to a special or customized meaning. The term specifically may refer, without limitation, to a signal having a transient change in the amplitude of the signal from a first value, also denoted baseline value, to a second value, followed by a return to the baseline value or at least approximately to the baseline value. The second value may be a higher or lower value than the baseline value. A pulse duration may be ≤50 μs, preferably ≤20 μs, more preferably ≤10 μs. The duration of the single pulse must be sufficiently long to be able to record its propagation. The duration of the single pulse must be preferentially short, in order to not excite the system electrochemically. The fast-transient voltage signal may be applied during at least one test sequence, for example, a time sequence. The fast-transient voltage signal may be applied repeatedly, in particular periodically. The time distance between the cycles must be sufficiently long in order to keep the system at its steady-state. The fast-transient voltage signal may comprise a repeatable cycle, wherein the repeatable cycle comprises at least one signal flank. The pulse may comprise two edges: the leading edge or front edge, which is the first edge of the pulse and the trailing edge or back edge, which is the second edge of the pulse.

The terms first and second "value" may refer to regions or points of the fast-transient voltage, in particular its amplitude. The first value may be the baseline value. The first value may be a local and/or overall minimum of the fast-transient voltage signal. The first value may be a first plateau of the fast-transient voltage signal. The first value may refer to a time point with no voltage is applied to the measurement electrodes. The first value may be the DC polarization voltage of the analyte sensor. The second value may be a local and/or overall extremum of the fast-transient voltage signal. The second value may be a second plateau of the fast-transient voltage signal, which may be reached during application of the fast-transient voltage. The second value may be extremum of the fast-transient voltage signal.

The term "signal flank" as used herein is a broad term and is to be given its ordinary and customary meaning to a person of ordinary skill in the art and is not to be limited to a special or customized meaning. The term specifically may refer, without limitation, to transition of a signal amplitude from low to high signal value or from high to low signal value. The signal flank may be a rising signal flank or a falling signal flank. The signal flank of the fast-transient voltage signal may have a change in signal from the first value of the signal flank to the second value of the signal flank in a microsecond to nanosecond range. The signal flank of the fast-transient voltage signal may have a change in signal from the second value of the signal flank to the first value of the signal flank in a microsecond to nanosecond range. The signal flank may also be referred to as edge.

The fast-transient voltage may have a low-to-high transition of a signal amplitude, which is equivalent to rising or positive signal flank, or high-to-low transition of a signal amplitude, which is equivalent to falling or negative signal flank. The fast-transient voltage may have steep edges. The signal flank, in particular edge, of the fast-transient voltage may have a change from the first value to the second value in a microsecond to nanosecond range. The signal flank of the fast-transient voltage may have a change from the second value to the first value in a microsecond to nanosecond range. Specifically, the fast transition square wave may have a change in voltage from the first value to the second value below or equal 50 ns, preferably below or equal 20 ns. The change in voltage from the first value to the second value may be even faster and may be only limited by electronics such as by a fast-transient voltage generator (DAC, DO or others) or a read-out unit (voltage amplifier, ADC, or others). The faster the change of voltage (higher slew rate) and the sharper the transition to the plateau, the more precise the membrane property can be determined.

The term "fast-transient" as used herein is a broad term and is to be given its ordinary and customary meaning to a person of ordinary skill in the art and is not to be limited to a special or customized meaning. The term specifically may refer, without limitation, to time range between first and second values of the signal flank. The fast-transient voltage signal may have a rising signal flank and a falling signal flank. The fast-transient voltage signal may have steep edges. Specifically, the fast transition square wave may have a change in signal from the first value of the signal flank to the second value of the signal flank below or equal 50 ns, preferably below or equal 20 ns. The change in signal from the first value of the signal flank to the second value of the signal flank may be even faster and may be only limited by electronics such as by an analog-to-digital-converter. The faster the flank and the sharper the transition to the plateau, the more resolution may be between the ohmic part of the system resistance and the capacitive part of the system capacitance.

The constant voltage may be different to the fast-transient voltage signal. In particular, the constant voltage may be longer compared to the fast-transient voltage signal. The constant voltage may be a permanent signal, not a pulsed one. The fast-transient voltage signal may be a voltage pulse with high frequency that only characterizes the capacitive and ohmic parts of the electrochemical cell. Therefore, the constant voltage and the fast-transient voltage signal may not influence each other, since they have completely different time domains.

The duration of the single fast-transient voltage must be sufficiently long to record the response voltage. The duration of the single fast-transient voltage must be sufficiently short, in order to avoid the system perturbation as explained above.

Without wishing to being bound by theory, the fast-transient voltage or the voltage pulse is so short, in particular ultrashort, that no faradaic currents are generated and that an electrochemical system of the analyte sensor is not disturbed and brought out of equilibrium. The ultrashort voltage of the fast-transient voltage for determining the membrane property may allow that a measurement signal for determining the analyte concentration can be undisturbed determined. The ultrashort voltage signal may prevent that side reaction occur. Moreover, the method according to this disclosure may allow to stay in the so-called time domain such that there is no need to transform to the so-called frequency domain.

An amplitude of the fast-transient voltage may vary in a broad range and must be optimized for a given set-up. Generally, the lower limit may be limited by the readout technique, which must record the response voltage, mostly by its input range and resolution and may require an additional sufficiently fast voltage amplifier.

The fast-transient voltage may comprise a repeatable cycle, wherein the repeatable cycle comprises at least one signal edge. The fast-transient voltage may be applied during at least one test sequence, for example, a time sequence. The fast-transient voltage signal may be applied repeatedly, in particular periodically. The interval between the cycles may be sufficiently long in order to let the double layer capacitance and the shunt capacitor to recharge to their previous steady-state voltage. The discharge of these capacitances after stop of the fast-transient voltage applying, as described above, means current flow opposite to the first response signal and thus distortion of the signal.

The fast-transient voltage may be applied repeatedly to the measurement electrodes, in particular in time intervals from minutes to seconds. For example, the fast-transient voltage signal may be applied repeatedly in 5 minutes-intervals.

The fast-transient voltage signal may be generated by at least one signal generator device, in particular of the controlling unit such of the MCU. The term "signal generator device" generally refers to a device, for example, a voltage source, being configured to generate a voltage signal. The "signal generator device" may also be referred to as "voltage generating device." The signal generator device may comprise at least one voltage source. The signal generator device may comprise at least one function generator selected from the group consisting of: at least one square wave generator and at least one sine wave generator. The signal generator device may also generate a single pulse which may be unsymmetrically. "Unsymmetrically" in this context means that a first pulse may be different from a second pulse and/or a third pulse and/or any other subsequent pulse. The signal generator device may be part of measurement electronics of the analyte sensor and/or may be connected to the analyte sensor and may be designed as a separate device. The signal generator device may be configured for applying the fast-transient voltage signal to the measurement electrodes. The fast-transient voltage signal may be applied to at least two measurement electrodes in at least one signal application step.

The term "applying the fast-transient voltage signal to the measurement electrodes" as used herein is a broad term and is to be given its ordinary and customary meaning to a person of ordinary skill in the art and is not to be limited to a special or customized meaning. The term specifically may refer, without limitation, to applying the fast-transient voltage signal to one of the measurement electrodes, in particular to the working electrode.

Step ii) further may comprise measuring a first membrane response signal with both the serial resistors $R_3$, $R_4$ as reference and measuring at least one second membrane response signal between the serial resistors $R_3$, $R_4$ with one of the serial resistors $R_3$, $R_4$ as reference. The term "membrane response signal" as used herein is a broad term and is to be given its ordinary and customary meaning to a person of ordinary skill in the art and is not to be limited to a special or customized meaning. The term specifically may refer, without limitation, to measured propagation of the applied fast-transient voltage signal. The terms "membrane response signal" and "propagation" are used herein as synonyms. The membrane response signal may be a change of the applied fast-transient voltage signal. The membrane response signal may directly or indirectly refer to equivalent series resistance of the analyte sensor. The membrane response signal may be the ohmic and capacitive characterization of the analyte sensor in its in-vivo surroundings. In particular, the membrane response signal does not relate to current response.

In a two-electrode sensor, the constant voltage and the fast-transient voltage may be applied to the same or different measurement electrodes. In a three-electrode system the constant potential difference may be determined and controlled between the working electrode and the reference electrode. In order to achieve this, the potentiostat may regulate the voltage between reference electrode and counter electrode. Thus, the potential of the working electrode may be determined vs. the reference electrode, but the potential of the working electrode may be regulated via the working-electrode-counter-electrode-voltage. The fast-transient voltage signal can be applied between counter electrode and working electrode or between working electrode and reference electrode or counter electrode and reference electrode.

The failure detection resistors may be selected suitable for determining a value to be measured such as the electrical resistance of the membrane element. The failure detection resistors must reflect the measurement range of the membrane element. The failure detection resistors may reflect required measurement tolerances which must be maintained for correct membrane element resistances.

The fast-transient voltage amplitude may be determined by using the failure detection resistors. Before the application of the fast-transient voltage the potentiostat determines the base voltage only. During the application of fast-transient voltage, the potentiostat determines the sum of the base voltage signal and the fast-transient voltage signal. The potentiostat may be configured for determining the propagation of the fast-transient voltage signal applied to the working electrode. The potentiostat may be configured for determining a change or difference $\Delta V_{ex}$ of the measurement voltage signal at the working electrode before application of the fast-transient voltage signal and during the application of the fast-transient voltage signal. The potentiostat may be configured for determining a change or difference $\Delta V_{prop}$ of voltage at the failure detection resistors before application of the fast-transient voltage signal and during the application of the fast-transient voltage signal.

The serial resistors $R_3$, $R_4$ may be arranged as follows. A first one of the serial resistors, e.g., $R_3$, may be connected to the signal generator device and to the other serial resistor, such as $R_4$. The other serial resistor may be connected to the working electrode and thus, to the membrane element. As outlined above, step ii) further may comprise measuring a first membrane response signal with both the serial resistors $R_3$, $R_4$ as reference and measuring at least one second membrane response signal between the serial resistors $R_3$, $R_4$ with one of the serial resistors $R_3$, $R_4$ as reference. As outlined above, the fast-transient voltage may be generated by using the signal generator device. The continuous analyte monitoring system may comprise a further resistance connected to signal the DAC or PWM configured for preventing that the fast-transient voltage is short-circuit by the output of the DAC or PWM. The continuous analyte monitoring system may comprise at least one capacitor acting like short circuits for the rising edge of the pulse. So right after the rising edge of the pulse, an equivalent circuit seeing by the signal generator device can be regarded as made of three resistors in serial, namely $R_3$, $R_4$ and $R_{mem}$. The continuous analyte monitoring system, in particular the MCU, may comprise at least one second ADC channel (ADC2) arranged between the working electrode and an input of the serial resistor $R_4$. The continuous analyte monitoring system, in particular the MCU, may comprise at least one third ADC channel (ADC3) arranged between the serial resistors $R_3$ and $R_4$. The continuous analyte monitoring system, in particular the MCU, may comprise at least one fourth ADC channel (ADC4) arranged between the signal generator device and an input of the serial resistor $R_3$. By measuring the voltage with ADC2 and ADC4 and thus with both the serial resistors $R_3$, $R_4$ as reference before and after the rising edge of the pulse, it may be possible to calculate the value of a first membrane resistance $R_{mem,1}$, e.g., by $$R_{mem,1} = (R_3 + R_4) \cdot [(ADC2a - ADC2b)/((ADC4a - ADC4b) - (ADC2a - ADC2b))],$$

with ADC2$b$ is the voltage converted by ADC2 before the rising edge of the pulse, ADC2$a$ is the voltage converted by ADC2 after the rising edge of the pulse, ADC4$b$ is the voltage converted by ADC4 before the rising edge of the pulse, ADC4$a$ is the voltage converted by ADC4 after the rising edge of the pulse.

By measuring the voltage with ADC3 and ADC4 and thus with the serial resistors $R_3$ as reference before and after the rising edge of the pulse, it may be possible to calculate the value of $R_{mem} + R_4$, and therefrom a second membrane resistance $R_{mem,2}$, e.g., by $$R_{mem,2} = (R_3 \cdot [(ADC3a - ADC3b)/((ADC4a - ADC4b) - (ADC3a - ADC3b))]) - R_4,$$

with ADC3$b$ is the voltage converted by ADC3 before the rising edge of the pulse, ADC3$a$ is the voltage converted by ADC3 after the rising edge of the pulse, ADC4$b$ is the voltage converted by ADC4 before the rising edge of the pulse, ADC4$a$ is the voltage converted by ADC4 after the rising edge of the pulse.

Step iii) may comprise determining the first membrane resistance $R_{mem,1}$ by evaluating of the base voltage and the first membrane response signal and determining the second membrane resistance $R_{mem,2}$ by evaluating of the base voltage and the second membrane response signal.

Step iii) may further comprise comparing the first membrane resistance $R_{mem,1}$ and the second membrane resistance $R_{mem,2}$. A failure may be detected if the first membrane resistance $R_{mem,1}$ and the second membrane resistance $R_{mem,2}$ deviate from one another more than the predetermined tolerance. For example, the predetermined tolerance may be ±5%, preferably ±2%. Thus, if both of the values of the membrane resistance are the same within tolerances the membrane element is functional.

With respect to determining the membrane resistance reference is further made to European Patent Application No. 20 162 098.6 filed on Mar. 10, 2020, the content of which is included herein by reference.

The method may comprise detection a failure of other components of the continuous analyte monitoring system such as of the signal generator device, the DAC or PWM and/or of at least one ADC channel. For example, the DAC or PWM may be tested using ADC2, ADC3 and ADC4 channels. If no failure is detected, the electronics is fully functional.

In a further aspect, a method for determining a concentration of at least one analyte in body fluid using at least one continuous analyte monitoring system is disclosed. The method comprises detecting a failure of at least one component of the continuous analyte monitoring system according to this disclosure and according to one or more of the embodiments of the method as disclosed above or as disclosed in further detail below. The method comprises at least one analyte measurement step. In the measurement step the concentration of the analyte is determined.

For definitions of the features of the method and for optional details of the method for determining the concentration of the analyte, reference may be made to one or more of the embodiments of the method for detecting a failure of at least one component of the continuous analyte monitoring system as disclosed above or as disclosed in further detail below.

The term "determining a concentration of at least one analyte" generally refers to a quantitative detection of the at least one analyte. As a result of the determination, at least one signal, such as at least one measurement signal, and/or at least one measurement value may be produced and/or provided which characterizes an outcome of the determination. The signal specifically may be or may comprise at least one electronic signal such as at least one voltage and/or at least one current. The at least one signal may be or may comprise at least one analogue signal and/or may be or may comprise at least one digital signal.

As outlined above, the method comprises at least one analyte measurement step. In the analyte measurement step the constant voltage may be applied to the working electrode such that a constant potential may be applied between the working electrode and the counter electrode such that a current produced at the working electrode flows towards the counter electrode. The current may be measured at the counter electrode using I/U converter and an analog to digital converter (ADC) channel. The method furthermore may comprise at least one evaluation step, wherein current is evaluated. At least one evaluation device may be used for evaluating the measured current and for determining the concentration of the analyte therefrom. As used herein, the term "evaluation device" generally refers to an arbitrary device being configured to derive at least one item of information from data. The evaluation device may be configured to derive the at least one item of information regarding the presence and/or concentration of the analyte in the body fluid from the current. As an example, the evaluation device may be or may comprise one or more data processing devices, such as one or more computers, preferably one or more microcomputers and/or microcontrollers. The evaluation device may comprise one or more integrated circuits, such as one or more application-specific integrated circuits (ASICs). Additional components may be comprised, such as one or more preprocessing devices and/or data acquisition devices, such as one or more devices for receiving and/or preprocessing of the electrode signals, such as one or more converters and/or one or more filters. Further, the evaluation device may comprise one or more data storage devices. Further, as outlined above, the evaluation device may comprise one or more interfaces, such as one or more wireless interfaces and/or one or more wire-bound interfaces. The evaluation device may be a part of sensor electronics of the continuous analyte monitoring system. The continuous analyte monitoring system may be configured for communicating with a further device such as for providing and/or presenting at least one failure detection notification and/or measurement results. The further device may be or comprise a microprocessor, a cellular phone, a smart phone, a personal digital assistant, a personal computer, or a computer server.

This disclosure further discloses and proposes a computer program including computer-executable instructions for performing the method for determining a concentration of at least one analyte and/or the method for detecting a failure of at least one component of the continuous analyte monitoring system according to this disclosure in one or more of the embodiments enclosed herein, when the program is executed on a computer or computer network. Specifically, the computer program may be stored on a computer-readable data carrier. Thus, specifically, one, more than one or even all of method steps, as indicated above, may be performed by using a computer or a computer network, preferably by using a computer program.

This disclosure further discloses and proposes a computer program product having program code means, in order to perform the method for determining a concentration of at least one analyte and/or the method for detecting a failure of at least one component of the continuous analyte monitoring system according to this disclosure in one or more of the embodiments enclosed herein, when the program is executed on a computer or computer network. Specifically, the program code means may be stored on a computer-readable data carrier.

Further, this disclosure discloses and proposes a data carrier having a data structure stored thereon, which, after loading into a computer or computer network, such as into a working memory or main memory of the computer or computer network, may execute the methods according to one or more of the embodiments disclosed herein.

This disclosure further proposes and discloses a computer program product with program code means stored on a machine-readable carrier, in order to perform at least one of the methods according to one or more of the embodiments disclosed herein, when the program is executed on a computer or computer network. As used herein, a computer program product refers to the program as a tradable product. The product may generally exist in an arbitrary format, such as in a paper format, or on a computer-readable data carrier. Specifically, the computer program product may be distributed over a data network.

Finally, this disclosure proposes and discloses a modulated data signal which contains instructions readable by a computer system or computer network, for performing the methods according to one or more of the embodiments disclosed herein.

Preferably, referring to the computer-implemented aspects of this disclosure, one or more of the method steps or even all of the method steps of at least one of the methods according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

Specifically, this disclosure further discloses:

A computer or computer network comprising at least one processor, wherein the processor is adapted to perform at least one of the methods according to one of the embodiments described in this description, a computer loadable data structure that is adapted to perform at least one of the methods according to one of the embodiments described in this description while the data structure is being executed on a computer, a computer program, wherein the computer program is adapted to perform at least one of the methods according to one of the embodiments described in this description while the program is being executed on a computer, a computer program comprising program means for performing at least one of the methods according to one of the embodiments described in this description while the computer program is being executed on a computer or on a computer network, a computer program comprising program means according to the preceding embodiment, wherein the program means are stored on a storage medium readable to a computer, a storage medium, wherein a data structure is stored on the storage medium and wherein the data structure is adapted to perform at least one of the methods according to one of the embodiments described in this description after having been loaded into a main and/or working storage of a computer or of a computer network, and a computer program product having program code means, wherein the program code means can be stored or are stored on a storage medium, for performing at least one of the methods according to one of the embodiments described in this description, if the program code means are executed on a computer or on a computer network.

In a further aspect of this disclosure, a continuous analyte monitoring system for determining a concentration of at least one analyte in body fluid is disclosed. The continuous analyte monitoring system comprises at least one analyte sensor having at least two measurement electrodes. The continuous analyte monitoring system comprises at least one component and at least one failure detection resistor. The continuous analyte monitoring system comprises at least one controlling unit. The controlling unit is configured for applying a constant voltage between the measurement electrodes and for measuring at least one first response signal. The controlling unit is configured for applying a failure detection signal distinguishable from the constant voltage and/or from the first response signal in frequency and/or in height to the continuous analyte monitoring system and for measuring a response signal to the failure detection signal using the failure detection resistor. The controlling unit is configured for determining an information depending on at least one actual property of the component by evaluating the response signal. The controlling unit is configured for detecting a failure if the information deviates from at least one expected value more than at least one predetermined tolerance.

The analyte sensor may be a two electrode-sensor or a three electrode sensor. The measurement electrodes may be arranged on opposing sides of the analyte sensor.

The controlling unit may be or may comprise at least one microcontroller unit. The term "controlling unit" as used herein is a broad term and is to be given its ordinary and customary meaning to a person of ordinary skill in the art and is not to be limited to a special or customized meaning. The term specifically may refer, without limitation, to at least one unit of the continuous analyte monitoring system configured for controlling at least one function of the continuous analyte monitoring system such as regulating the potential, measuring current, providing a fast-transient voltage, or evaluation.

The continuous analyte monitoring system may be configured for performing the methods according to this disclosure. For definitions of the features of the continuous analyte monitoring system and for optional details of the continuous analyte monitoring system, reference may be made to one or more of the embodiments of the methods as disclosed above or as disclosed in further detail below.

Summarizing and without excluding further possible embodiments, the following embodiments may be envisaged:

Embodiment 1: A method for detecting a failure of at least one component of a continuous analyte monitoring system, wherein the continuous analyte monitoring system comprises the component and at least one failure detection resistor, wherein the continuous analyte monitoring system comprises at least one analyte sensor comprising at least two measurement electrodes, the method comprising the following steps:

i) applying a constant voltage between the at least two measurement electrodes of the analyte sensor and measuring a first response signal, ii) applying a failure detection signal distinguishable from the constant voltage and/or from the first response signal in frequency and/or in height to the continuous analyte monitoring system and measuring a second response signal to the failure detection signal using the failure detection resistor;

iii) determining an information depending on at least one actual property of the component by evaluating the first response signal and the second response signal, wherein a failure is detected if the information deviates from at least one expected value more than at least one predetermined tolerance.

Embodiment 2: The method according to embodiment 1, wherein the component is one or more of at least one measurement resistance of the continuous analyte monitoring system and/or at least one membrane element comprised by at least one of the measurement electrodes.

Embodiment 3: The method according to any one of embodiments 1 or 2, wherein the constant voltage is about 50 mV.

Embodiment 4: The method according to any one of embodiments 1 to 3, wherein the analyte sensor is a two-electrode sensor comprising two measurement electrodes or a three-electrode sensor comprising three measurement electrodes.

Embodiment 5: The method according to any one of embodiments 1 or 4, wherein the analyte sensor is an in vivo sensor.

Embodiment 6: The method according to any one of embodiments 1 to 5, wherein the method is performed in vivo.

Embodiment 7: The method according to embodiment 2, wherein the component is the at least one measurement resistance $R_1$, wherein step i) comprises applying the constant voltage between the measurement electrodes and determining a first current $I_1$ as first response signal using the measurement resistance $R_1$, wherein step ii) comprises applying a second current $I_2$ as failure detection signal to the continuous analyte monitoring system and measuring a resulting total current $I_{tot}$ as second response signal using the failure detection resistor $R_2$, wherein the second current $I_2$ is significantly smaller than the first current $I_1$, wherein in step iii) a failure is detected if the resulting total current $I_{tot}$ deviates more than the predetermined tolerance from a sum of the first current $I_1$ and the second current $I_2$.

Embodiment 8: The method according to embodiments 1 to 3, wherein the second current $I_2$ is around 5 nA or less.

Embodiment 9: The method according to embodiment 2, wherein the component is the membrane element, wherein the membrane element has a membrane resistance, wherein the continuous analyte monitoring system comprises at least two serial failure detection resistors $R_3$, $R_4$ in series with the membrane resistance, wherein step i) comprises measuring a base voltage as a first response signal of the continuous analyte monitoring system, wherein step ii) comprises generating at least one fast-transient voltage signal and applying the fast-transient voltage signal as a failure detection signal to the measurement electrodes, wherein step ii) further comprises measuring a first membrane response signal with both the serial resistors $R_3$, $R_4$ as reference and measuring at least one second membrane response signal between the serial resistors $R_3$, $R_4$ with one of the serial resistors $R_3$, $R_4$ as reference, wherein step iii) comprises determining a first membrane resistance $R_{mem,1}$ by evaluating of the base voltage and the first membrane response signal and determining a second membrane resistance $R_{mem,2}$ by evaluating of the base voltage and the second membrane response signal, wherein step iii) further comprises comparing the first membrane resistance $R_{mem,1}$ and the second membrane resistance $R_{mem,2}$, wherein a failure is detected if the first membrane resistance $R_{mem,1}$ and the second membrane resistance $R_{mem,2}$ deviate from one another more than the predetermined tolerance.

Embodiment 10: The method according to embodiment 9, wherein the fast-transient voltage signal has a square wave form or a sine wave signal form.

Embodiment 11: The method according to any one of embodiments 9 or 10, wherein the fast-transient voltage signal comprises a non-continuous signal such as a pulse, wherein a pulse duration is $\leq 20$ μs, preferably $\leq 10$ μs.

Embodiment 12: A method for determining a concentration of at least one analyte in body fluid using at least one continuous analyte monitoring system, wherein the method comprises detecting a failure of at least one component of the continuous analyte monitoring system according to any one of embodiments 1 to 11, wherein the method comprises at least one analyte measurement step, wherein in the measurement step the concentration of the analyte is determined.

Embodiment 13: A computer program comprising program means for performing the method according to any one of embodiments 1 to 11 and/or the method according to embodiment 12 while the computer program is being executed on a computer or on a computer network.

Embodiment 14: A continuous analyte monitoring system for determining a concentration of at least one analyte in body fluid, wherein the continuous analyte monitoring system comprises at least one analyte sensor having at least two measurement electrodes, wherein the continuous analyte monitoring system comprises at least one component and at least one failure detection resistor, wherein the continuous analyte monitoring system comprises at least one controlling unit, wherein the controlling unit is configured for applying a constant voltage between the measurement electrodes and for measuring at least one first response signal, wherein the controlling unit is configured for applying a failure detection signal distinguishable from the constant voltage and/or from the first response signal in frequency and/or in height to the continuous analyte monitoring system and for measuring a response signal to the failure detection signal using the failure detection resistor, wherein the controlling unit is configured for determining an information depending on at least one actual property of the component by evaluating the response signal, wherein the controlling unit is configured for detecting a failure if the information deviates from at least one expected value more than at least one predetermined tolerance.

Embodiment 15: The continuous analyte monitoring system according to embodiment 14, wherein the analyte sensor is a two electrode-sensor or a three electrode sensor.

Embodiment 16: The continuous analyte monitoring system according to any one of embodiments 14 or 15, wherein the measurement electrodes are arranged on opposing sides of the analyte sensor.

Embodiment 17: The continuous analyte monitoring system according to any one of embodiments 14 to 16, wherein the continuous analyte monitoring system is configured for performing the method according to any one of embodiments 1 to 11 and/or the method according to embodiment 12.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
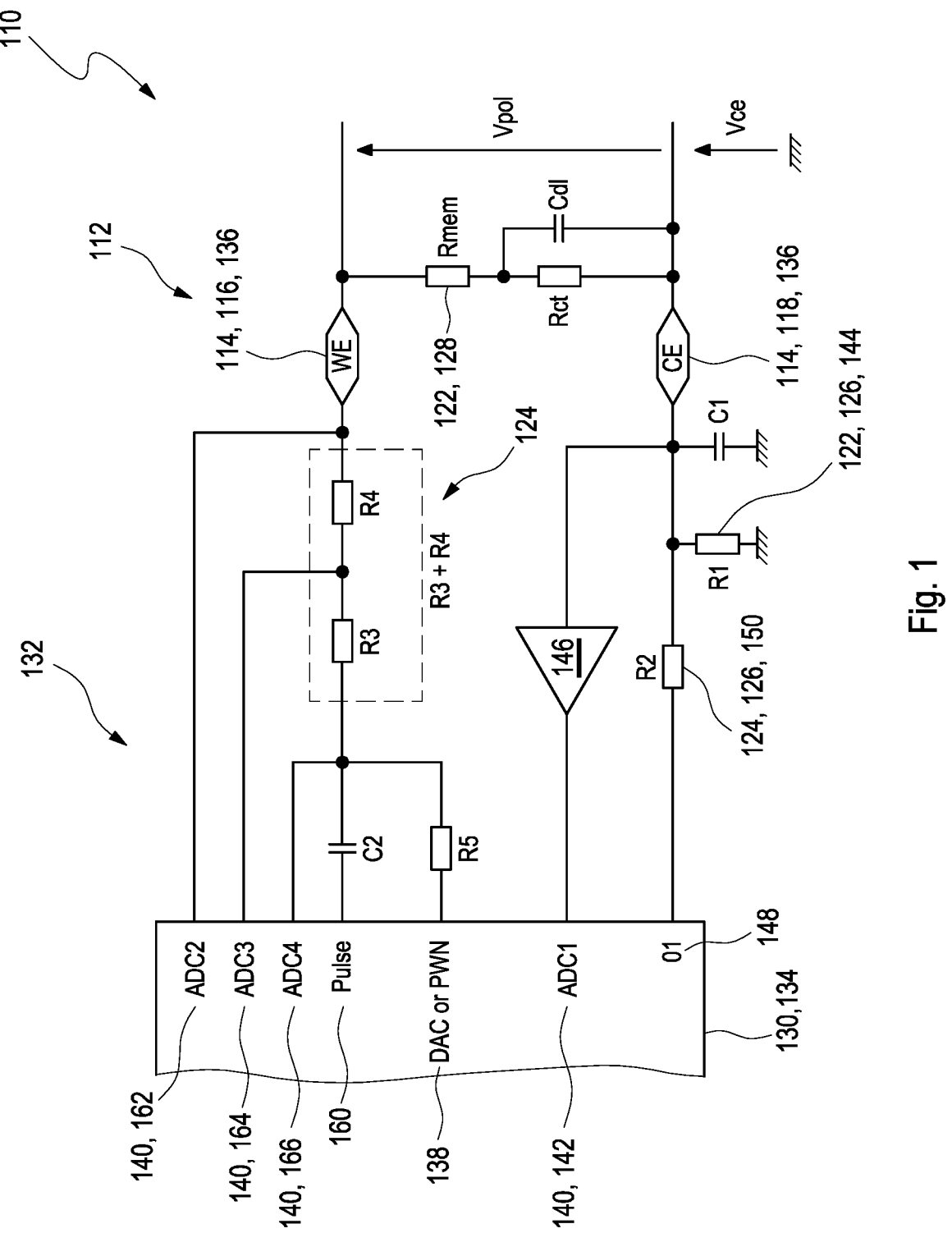
FIG. 1 shows an embodiment of an equivalent circuit of a continuous analyte monitoring system according to this disclosure for a two-electrode analyte sensor.

FIG. 1 shows an embodiment of an equivalent circuit of a continuous analyte monitoring system 110 according to this disclosure for a two-electrode sensor 112 comprising two measurement electrodes 114. The continuous analyte monitoring system is configured for determining a concentration of at least one analyte in body fluid. The analyte may be an arbitrary element, component or compound which may be present in a body fluid and the concentration of which may be of interest for a user. Specifically, the analyte may be or may comprise an arbitrary chemical substance or chemical compound which may take part in the metabolism of the user, such as at least one metabolite. As an example, the at least one analyte may be selected from the group consisting of glucose, cholesterol, triglycerides, lactate. Additionally or alternatively, however, other types of analytes may be determined and/or any combination of analytes may be determined. The body fluid may be a fluid, in particular a liquid, which may typically be present in a body or a body tissue of the user and/or which may be produced by the body of the user. Preferably, the body fluid may be selected from the group consisting of blood and interstitial fluid. However, additionally or alternatively, one or more other types of body fluids may be used, such as saliva, tear fluid, urine or other body fluids. During the detection of the at least one analyte, the body fluid may be present within the body or body tissue. Thus, the continuous analyte monitoring system 110 may, specifically, be configured for detecting the at least one analyte within the body tissue. The continuous analyte monitoring system 110 may be configured for continuously monitoring the analyte in the body fluid of the user. The continuous analyte monitoring system 110 or at least a part of the continuous analyte monitoring system 110 may remain in the body tissue of the user for a predetermined period of time, such as for several hours, specifically for one or more days, more specifically for up to one week, even more specifically for up to two weeks or even more.

The continuous analyte monitoring system 110 comprises the at least one analyte sensor 112 having at least two measurement electrodes 114. In the Figures, sensor contacts are denoted with reference number 114 for visualization. As the person skilled in the art immediately notices, these contacts are connected to the measurement electrodes 114. The analyte sensor 112 may be a sensor configured for detecting quantitatively or qualitative at least one analyte. The analyte sensor 112 may be or may comprise at least one electrochemical sensor. The electrochemical sensor may be based on electrochemical measurement principles, such as by using one or more of an amperometric, coulometric or a potentiometric measurement principle. Specifically, the electrochemical sensor may comprise at least one enzyme configured for performing at least one redox reaction in the presence of the analyte to be detected, wherein the redox reaction may be detected by electrical means. The detection of the analyte may comprise an electrochemical detection of an electrochemically detectable property of the analyte by electrochemical means, such as an electrochemical detection reaction. Thus, for example, the electrochemical detection reaction may be detected by comparing one or more electrode potentials, such as a potential of a working electrode 116 with the potential of one or more further electrodes such as a counter electrode 118 or a reference electrode 120. The detection may be analyte specific. The detection may be a qualitative and/or a quantitative detection.

The analyte sensor 112 may be an in-vivo sensor. The analyte sensor 112 may be configured for being at least partially implanted into a body tissue of a user. The analyte sensor 112 may be a subcutaneous analyte sensor. The analyte sensor 112 may be configured for implantation into a body tissue of the user. More specifically the analyte sensor 112 may be configured for continuous monitoring of the analyte. The analyte sensor 112 may be fully implantable or partially implantable.

Figure 3:
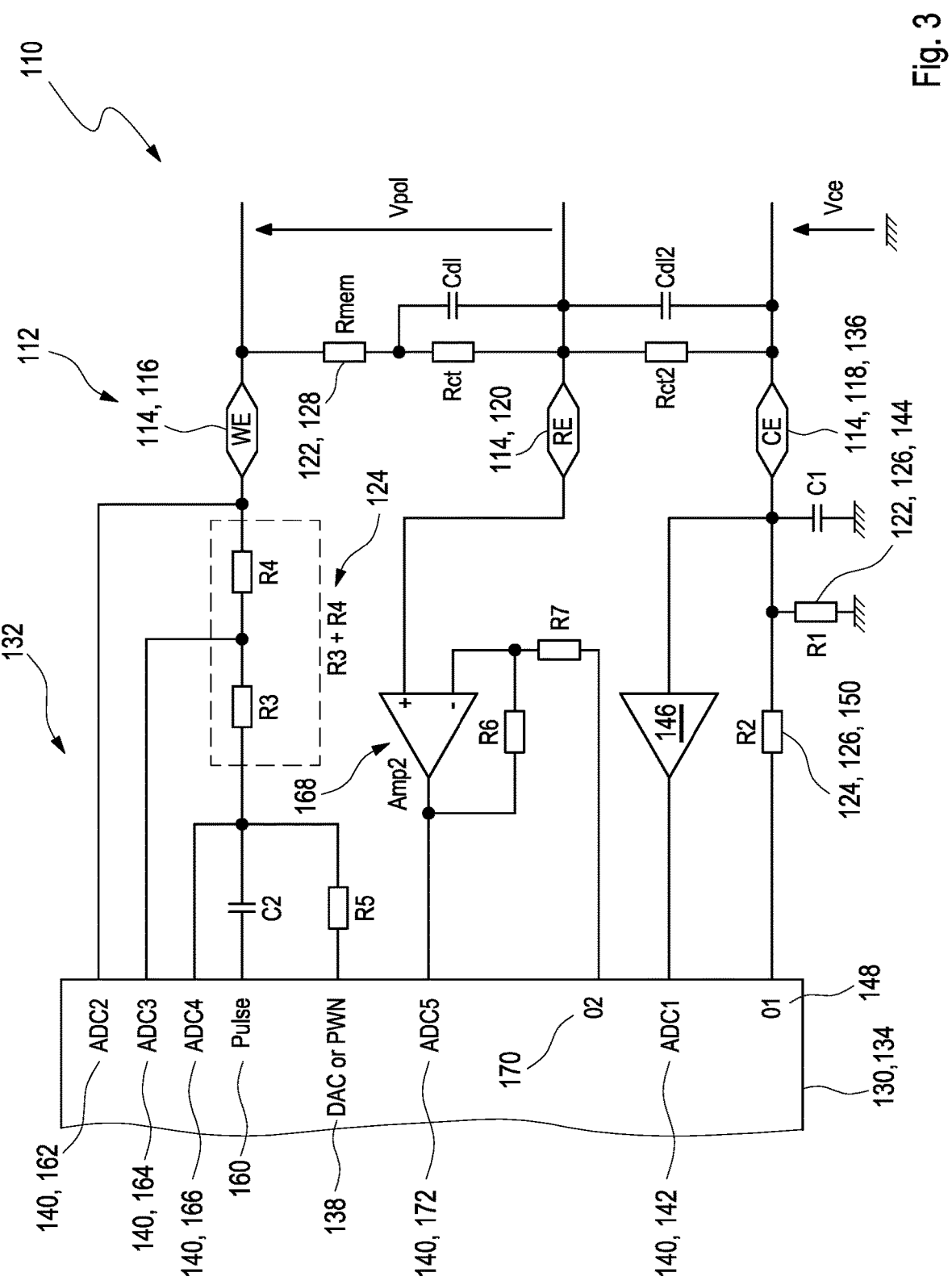
FIG. 3 shows a further embodiment of an equivalent circuit of the continuous analyte monitoring system according to this disclosure for a three-electrode analyte sensor.

The analyte sensor 112 may be a two-electrode sensor comprising two measurement electrodes 114, see FIG. 1, or a three-electrode sensor comprising three measurement electrodes 114, see FIG. 3. The measurement electrodes 114 may be electrodes which may be or can be brought in contact with an electrolyte, in particular with a body fluid. The at least two measurement electrodes 114 may be designed such that an electrochemical reaction may take place at one or more of the electrodes 114. Thus, the measurement electrodes 114 may be embodied such that an oxidation reaction and/or reduction reaction may take place at one or more of the electrodes 114.

One of the measurement electrodes 114 may be designed as working electrode 116. The working electrode 116 may be an electrode of the analyte sensor 112 which is configured for measuring a signal, such as a voltage, a current, a charge or electrical/electrochemical potential, dependent on the degree of an electrochemical detection reaction taking place at the working electrode 116, for the purpose of detecting the at least one analyte. The working electrode 116 may comprise at least one test chemical. The working electrode 116 may fully or partially be covered with at least one test chemical, specifically at least one test chemical comprising at least one enzyme for detecting the at least one analyte. As an example, glucose oxidase (GOx) or glucose dehydrogenase (GDH) may be used. The test chemical, further, may comprise additional materials, such as binder materials, electrode particles, mediators or the like. Thus, as an example, the test chemical may comprise at least one enzyme, carbon particles, a polymer binder and $MnO_2$ particles. In another preferred embodiment, the test chemical may comprise an enzyme and a mediator polymer comprising a polymeric material and a metal containing complex, for example, a modified poly(vinylpyridine) backbone loaded with poly(bi-imidizyl) Os complexes covalently coupled through a bidentate linkage. Further, the at least one test chemical may be comprised in a single layer, or the test chemical may comprise a plurality of layers, such as one layer having the at least one enzyme and one or more additional layers having one or more additional functions, such as one or more diffusion barriers and/or one or more biocompatibility layers.

The other one of the measurement electrodes 114 may be designed as counter electrode 118 or auxiliary electrode. The counter electrode 118 may be an electrode adapted for performing at least one electrochemical counter reaction and/or configured for balancing a current flow due to the detection reaction at the working electrode 116. The counter electrode 118 may be a part of the implanted or partially implanted analyte sensor 112, or may be an individual electrode, which is either implanted or partially implanted or placed somewhere else on the body, e.g., on the skin surface. In case of the analyte sensor 112 comprises a two-electrode system as comprising precisely two measurement electrodes 114, the counter electrode 118 may complete the circuit such that charge can flow through an electrochemical cell given by the working electrode 116, the counter electrode 118 and an electrolyte, such as the body fluid, and may maintain a constant counter electrode potential, also referred to as a constant reference potential, regardless of current. The working electrode 116 may have a higher potential compared to the other one of the measurement electrodes of the analyte sensor 112, which is also denoted counter electrode 118.

Additionally, as shown in FIG. 3, the analyte sensor 112 may comprise the at least one reference electrode 120. The reference electrode 120 may be an electrode of the analyte sensor which is configured to provide an electrochemical reference potential which, at least widely, is independent of the presence or absence or concentration of the analyte. The reference electrode 120 may be configured for being a reference for measuring and/or controlling a potential of the working electrode 116. The reference electrode 120 may have a stable and well-known electrode potential. The electrode potential of the reference electrode 120 may preferably be highly stable. One of the measurement electrodes 114 may have several functionalities, as for instance, combined reference and counter electrode, which has both, the function of the reference and counter electrode, which means it provides a reference potential and balances the current flow from the working electrode 116.

The continuous analyte monitoring system 110 comprises at least one component 122 and at least one failure detection resistor 124. The component 122 may be one or more of at least one measurement resistance 126 configured for measurement of a sensor current of the continuous analyte monitoring system 110 and/or at least one membrane element 128 (showing as equivalent resistance in FIGS. 1 and 3) comprised by at least one of the measurement electrodes 114. The failure detection resistor 124 may be at least one resistor which can be used for failure detection. The failure detection resistor 124 may have a known, such as predetermined or preknown, resistance value. The resistance value may be an average value determined, specifically pre-determined, from a plurality of reference measurements. The resistance value may be selected suitable for determining the failure of the respective component such as of the measurement resistance or the membrane element. The failure may be a deviation from a target value and/or a target behavior. The failure specifically may refer to a functional failure. The failure may occur due to short circuit, cracking in the component, aging or the like and may result in false or incorrect detection of the analyte.

The continuous analyte monitoring system 110 comprises at least one controlling unit 130, also referred to as a "controller." The controlling unit 130 may be or may comprise at least one microcontroller unit. The controlling unit 130 may be at least one unit of the continuous analyte monitoring system 110 configured for controlling at least one function of the continuous analyte monitoring system such as regulating the potential, measuring current, providing a fast-transient voltage, or evaluation.

The controlling unit 130 is configured for applying a constant voltage between the measurement electrodes 114 and for measuring at least one first response signal. The constant voltage may be a constant potential difference or polarizing potential of arbitrary height in between the two measurement electrodes 114. For example, the counter electrode 118 may be grounded and the constant voltage may be applied to the working electrode 116. For example, the constant voltage may be about 50 mV. The first response signal may be at least one current signal or at least one voltage signal generated by the analyte sensor 112 in a situation of a constant voltage between the at least two measurement electrodes 114. Other values of constant voltage may be possible. The constant voltage may depend on chemistry at the measurement electrodes. Selecting suitable constant voltage depending on the chemistry at the measurement electrodes is known to the person skilled in the art.

The analyte sensor 112 may comprise and/or may be connected to at least one measuring device and/or may be part of at least one measuring device, in particular at least one potentiostat 132 or galvanostat, configured for detecting the at least one analyte. Operating principles of potentiostats and galvanostats are generally known to the person skilled in the art. The potentiostat 132 may be configured for generating and/or applying the constant voltage. By applying a constant voltage a constant potential difference between the measurement electrodes 114 may be achieved. The constant potential difference may also be referred to as polarization voltage of the analyte sensor 112. In the situation of a constant potential difference between the measurement electrodes 114, a current that is proportional to the level of glucose present into the body of the user may be flowing into the working electrode 116 and outside of the counter electrode 118. The constant voltage may a continuous direct current (DC) signal which polarizes an electrochemical cell of the analyte sensor 112, and serves as the "motor" for the amperometric measurement of the analyte oxidized by GOx. The constant voltage may be adjusted from time to time or continuously in order to give the analyte sensor 112 its polarization voltage, preferably, in order to keep the predefined polarization voltage at the analyte sensor 112.

In particular, the potentiostat 132 may be configured for monitoring and maintaining a potential applied at the working electrode 116. The potentiostat 132 may be configured for monitoring and maintaining the potential between the reference electrode 120 and the working electrode 116. In FIG. 3, the potentiostat 132 may be configured for monitoring and maintaining the potential between the combined counter-reference electrode 118, 120 and the working electrode 116. The potentiostat 132 may be configured for maintaining the desired polarization voltage, for example, 50 mV, between the counter electrode 118 and the working electrode 116 or between the working electrode 116 and the combined counter-reference electrode 118, 120. The current flowing between working electrode 116 and counter electrode 118 or combined counter-reference electrode 118, 120 may be measured at the working electrode 116 or counter electrode 118 or combined counter-reference electrode 118, 120. The reference electrode 120 may be used to monitor the potential of the working electrode 116.

The controlling unit 130 may a digital controlling unit such as at least one microcontroller unit (MCU) 134. The MCU 134 may be configured for regulating the voltage between the measurement electrodes 114. The analyte sensor 112 may comprise the MCU 134 and/or may be directly connectable to the MCU 134. For example, the analyte sensor 112 may comprise sensor contacts 136 via which the analyte sensor 112, in particular the measurement electrodes 114 can be connected to the MCU 134. Usage of an MCU 134 has several advantages. Specifically, only very few analogue components are required. Moreover, there is no need for any voltage regulator or additional voltage reference. The MCU 134 may comprise a Digital to Analog converter (DAC) or at least one Pulse Width Modulator (PWM) 138 which is configured for applying the constant voltage to the measurement electrodes 114. The MCU 134 may comprise a plurality of Analog to Digital channels (ADC) 140. The MCU 134 may comprise at least one first ADC channel (ADC1) 142 for determining voltage output at the counter electrode 118. The potential at the counter electrode 118 may be measured and therefore known from the MCU 134. The MCU 134 is configured for measuring the potential at the counter electrode 118 via the first ADC channel 142 and to adjust the DAC or PWM 138 in order to get the pre-defined polarization of the measurement electrodes 114.

The continuous analyte monitoring system 110 may comprise the at least one measurement resistance 126 used for measuring the current flowing outside of the counter electrode 118. The continuous analyte monitoring system 110 may comprise at least one first measurement resistance 144 which may be configured for converting the current flowing out of the counter electrode 118 into a voltage proportional to the current. The MCU 134 may be connected to at least one amplifier 146 such as an operational amplifier. The amplifier may be configured for amplifying the voltage, such as by a constant gain factor, before measurement at the first ADC channel 142. For example, the constant gain may be 45. The MCU 134 may further comprise at least one output (O1) 148 which, for detection of the analyte, may be put at ground, i.e., logical 0. The continuous analyte monitoring system 110 may comprise at least one second measurement resistance 150 in parallel to the first measurement resistance 144 and connected to the output in case of being at logical 0. The second measurement resistance 150 may have a resistance much higher than the first measurement resistance 144. Thus, the current from the counter electrode 118 may be flowing into the first measurement resistance 144 and the second measurement resistance 150. If those two measurement resistances 144, 150 would have known and unchanged values, it would be possible to calculate the current flowing out of the counter electrode 118 using the ADC1 142 channel by using Ohm's law.

The controlling unit 130 is configured for applying a failure detection signal distinguishable from the constant voltage and/or from the first response signal in frequency and/or in height to the continuous analyte monitoring system 110 and for measuring a response signal to the failure detection signal using the failure detection resistor 124. The failure detection signal may be a current or voltage signal distinguishable from the constant voltage and/or from the first response signal in at least one property which can be used for detecting the failure of the component. The failure detection signal is distinguishable from the constant voltage and/or from the first response signal in frequency and/or in height. For example, the failure detection signal may be significantly smaller than the constant voltage and/or the first response signal. For example, the failure detection signal may be significantly shorter such as a pulse than the constant voltage. The second response signal may be at least one current signal or at least one voltage signal determined using the failure detection resistor 124 in response to application to the failure detection signal. Specifically, the second response signal may be measurable by using the failure detection resistor 124.

The controlling unit 130 is configured for determining an information depending on at least one actual property of the component 122 by evaluating the response signal. The property of the component 122 may be at least one arbitrary property of the component 122 influencing the analyte detection. For example, the component 122 may be a measurement resistance 126 and the property may be a resistance value. For example, the component may be a membrane element 128 comprised by at least one of the measurement electrodes 114 and the property may be at least one membrane property. The actual property may be a current property of the component 122, which may depend on a status or a condition of the component 122. The status or condition of the component 122 may change during time such as due to aging, mechanical influences, temperature influences and the like. The information depending on the actual property may be an arbitrary information indicating status or condition of the component 122.

The controlling unit 130 is configured for detecting a failure if the information deviates from at least one expected value more than at least one predetermined tolerance. The expected value may be a target value of the component 122. For example, a failure may be detected if the information deviates from at least one expected value more than ±10%, preferably ±5%, more preferably ±2%.

Figure 2:
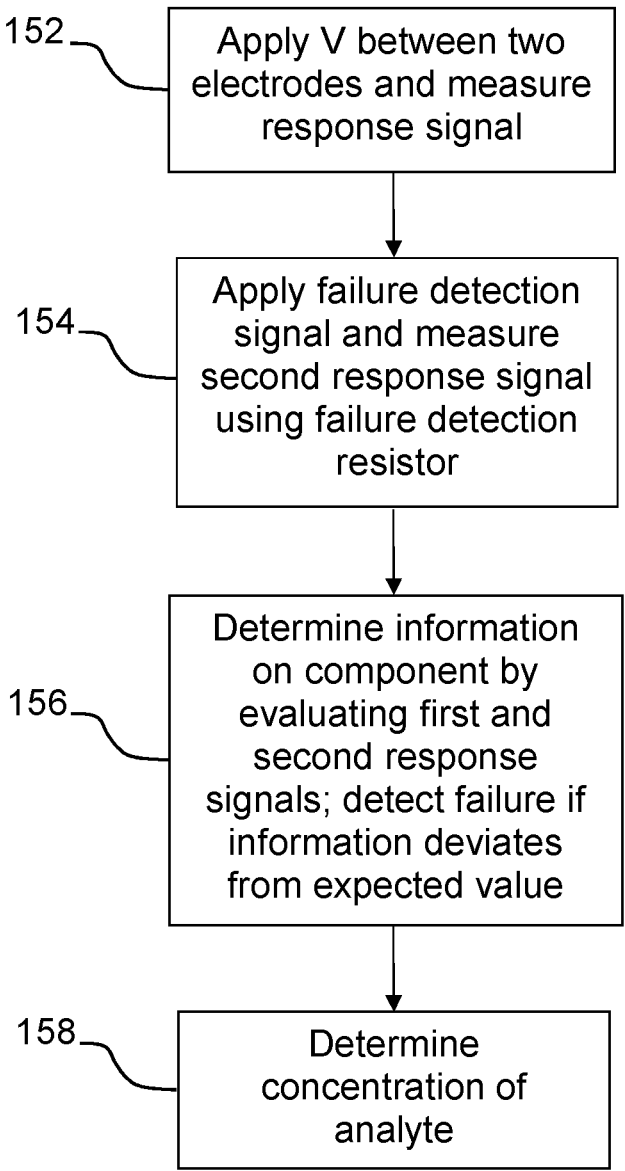
FIG. 2 shows a flow chart of an embodiment of a method for detecting a failure of at least one component of a continuous analyte monitoring system and a method for determining a concentration of at least one analyte in body fluid using at least one continuous analyte monitoring system.

FIG. 2 shows a flow chart of an embodiment of a method for detecting a failure of at least one component 122 of the continuous analyte monitoring system 110 and a method for determining a concentration of at least one analyte in body fluid using the at least one continuous analyte monitoring system 110.

The methods comprise the following method steps:

i) (denoted with reference number 152) applying a constant voltage between the at least two measurement electrodes 114 of the analyte sensor 112 and measuring the first response signal, ii) (denoted with reference number 154) applying the failure detection signal distinguishable from the constant voltage and/or from the first response signal in frequency and/or in height to the continuous analyte monitoring system 110 and measuring the second response signal to the failure detection signal using the failure detection resistor 124;

iii) (denoted with reference number 156) determining an information depending on at least one actual property of the component by evaluating the first response signal and the second response signal, wherein a failure is detected if the information deviates from at least one expected value more than at least one predetermined tolerance.

Moreover, the method for determining the concentration of the analyte comprises at least one analyte measurement step 158. In the measurement step the concentration of the analyte is determined.

Examples of the method steps i) to iii) will be further described with respect to FIGS. 1 and 3 in the following.

For example, the component 122 may be at least one of the measurement resistances 126 of the continuous analyte monitoring system 110. The measurement resistance 126 may be a resistor which can be used for determining the current flowing out of the counter electrode 118. The measurement resistance 126 can be used for measurement of a sensor current of the continuous analyte monitoring system. As outlined above, the continuous analyte monitoring system 110 may comprise a measurement resistance 126 which may be connected to the counter electrode 118 and which may be configured for converting the current flowing out of the counter electrode 118 into a voltage proportional to the current. As further outlined above, the MCU 134 may further comprise the at least one output 148 which, for detection of the analyte, may be put at ground, i.e., logical 0. The continuous analyte monitoring system 110 may comprise the at least one second measurement resistance 150 in parallel to the first measurement resistance 144 and connected to the output 148 in case of being at logical 0. The second measurement resistance 150 may have a resistance much higher than the first measurement resistance 144. Thus, the current flowing outside of the counter electrode 118 may be flowing into the first measurement resistance 144 and the second measurement resistance 150. The voltage proportional to the current flowing out of the counter electrode 118 may be measured, such as via the at last one ADC1 142 channel of the MCU 134. If the value of the first measurement resistance 144 and the second measurement resistance 150 would be known and unchanged, it would be possible to determine the current flowing into the first measurement resistance 144 from the measured voltage using Ohm's law.

The methods may comprise determining if the measurement resistances 126 are correctly working. The methods may comprise detecting if there is a failure in at least one of the measurement resistances 126, for example, in the first measurement resistance. For example, failure in at least one of the measurement resistances 126 may be detected using the second measurement resistance 150. Thus, the second measurement resistance 150 may be used as failure detection resistor 124.

Step i) may comprise applying the constant voltage between the measurement electrodes 114 and determining a first current $I_1$ as first response signal using the measurement resistance 126, in this example the first measurement resistance 144. Step ii) may comprises applying a second current $I_2$ as failure detection signal to the continuous analyte monitoring system 110 and measuring a resulting total current $I_{tot}$ as second response signal using the failure detection resistor 124. The second measurement resistance 150 may be a resistor arranged in parallel to the first measurement resistance 144. The resistance value of the failure detection resistor 124 may be higher than the resistance value of the first measurement resistance 144. For example, the resistance value of the failure detection resistor 124 may be around 100 times higher. A small additional current may injected into the first measurement resistance 144 by using the failure detection resistance 124. As outlined above, for detecting the at least one analyte, the output 148 normally may be put at ground, i.e., logical 0. For detecting the failure, a logical 1 may be put on the output 148 which results in adding a small current flowing over the failure detection resistor 126 into the first measurement resistance 144. This current may be dependent on the current already flowing from the analyte sensor 112 and on the values of the failure detection resistor 124 and the first measurement resistance 144. The second current $I_2$ may be significantly smaller than the first current $I_1$. For example, the second current $I_2$ may be around 5 nA or less, such as 3 nA.

In step iii) a failure may be detected if the resulting total current $I_{tot}$ deviates more than the predetermined tolerance from a sum of the first current $I_1$ and the second current $I_2$. For example, the predetermined tolerance may be ±5%, preferably ±2%. Specifically, as all values, the current values $I_1$, $I_2$ and $I_{tot}$ and the target value of the first measurement resistance 144 and of the failure detection resistor 124, are known it is possible to check if there is a failure. Thus, by first measuring before application of the additional current and in response to the additional current, it is possible to check if the measurement resistances 126 are working correctly. The proposed technique allows for testing the whole I to U converter, including the amplifier, and the resistors around it.

For example, the component 122 may be the membrane element 128 comprised by at least one of the measurement electrodes 114. For example, the membrane element 128 may be applied to the working electrode 116. The membrane element 128 may have at least one membrane property. Specifically, the membrane element 128 may have a membrane resistance. The membrane element 128 may comprise at least one polymer. The membrane element 128 may be applied to the working electrode 116 as thin polymer film. For example, the membrane element 128 may be or may comprise Poly-(4-(N-(3-sulfonatopropyl) pyridinium)-co-(4vinyl-pyridine)-co-styrene (5%/90%/5%) or hydrophilic Polyurethane such as HP60D20 available from Lubrizol®. For example, the membrane element 128 may comprise at least one of the following polymer classes and/or their copolymer: Poly(4 vinyl pyridine), Polymethacrylate, Polyacrylate, Polyvinyl pyrrolidone, Polyvinyl alcohol (PVA), Polyethylene glycol. The membrane property may be permeability of the membrane element 128. The permeability may be a material parameter characterizing transmission properties of the membrane element, specifically passing of substances through the membrane element 128. Further specifically, permeability may refer to permeability for a specific analyte since molecules and ions of the analytes may have different sizes, shapes and charge. In an embodiment, the permeability refers to the permeability of the membrane for glucose.

The continuous analyte monitoring system 110 may comprises at least two serial failure detection resistors 124 $R_3$, $R_4$ in series with the membrane resistance. Each of the two serial failure detection resistors 124 may have a known and/or pre-determined resistance value. Step i) may comprise measuring a base voltage as a first response signal of the continuous analyte monitoring system 110. The base voltage may a polarization of the analyte sensor due to the application of the constant voltage. Specifically, the base voltage corresponds to the constant voltage.

Step ii) may comprise generating at least one fast-transient voltage signal and applying the fast-transient voltage signal as a failure detection signal to the measurement electrodes 114. The fast-transient voltage may be at least one arbitrary voltage change in between the two measurement electrodes 114. The arbitrary voltage change may have fast transient signal flanks, in particular two very steep edges The fast-transient voltage may comprise a square wave form and/or a sine wave form. The fast-transient voltage may comprise a non-continuous signal such as a pulse. Specifically, the fast-transient voltage may comprise a fast transition square wave. The pulse may be a signal having a transient change in the amplitude of the signal from a first value, also denoted baseline value, to a second value, followed by a return to the baseline value or at least approximately to the baseline value. The second value may be a higher or lower value than the baseline value. A pulse duration may be ≤50 µs, preferably ≤20 µs, more preferably ≤10 µs. The duration of the single pulse must be sufficiently long to be able to record its propagation. The duration of the single pulse must be preferentially short, in order to not excite the system electrochemically. The fast-transient voltage signal may have a rising signal flank and a falling signal flank. The fast-transient voltage signal may have steep edges. Specifically, the fast transition square wave may have a change in signal from the first value of the signal flank to the second value of the signal flank below or equal 50 ns, preferably below or equal 20 ns. The change in signal from the first value of the signal flank to the second value of the signal flank may be even faster and may be only limited by electronics such as by an analog-to-digital-converter. The faster the flank and the sharper the transition to the plateau, the more resolution may be between the ohmic part of the system resistance and the capacitive part of the system capacitance.

The constant voltage may be different to the fast-transient voltage signal. In particular, the constant voltage may be longer compared to the fast-transient voltage signal. The constant voltage may be a permanent signal, not a pulsed one. The fast-transient voltage signal may be a voltage pulse with high frequency that only characterizes the capacitive and ohmic parts of the electrochemical cell. Therefore, the constant voltage and the fast-transient voltage signal may not influence each other, since they have completely different time domains.

The fast-transient voltage signal may be generated by at least one signal generator device (Pulse) 160, in particular of the MCU 134. The signal generator device 160 may be a voltage source, being configured to generate a voltage signal. The signal generator device 160 may comprise at least one voltage source. The signal generator device 160 may comprise at least one function generator selected from the group consisting of: at least one square wave generator and at least one sine wave generator. The signal generator device may also generate a single pulse which may be unsymmetrically. The signal generator device 160 may be part of measurement electronics of the analyte sensor and/or may be connected to the analyte sensor 112 and may be designed as a separate device. The signal generator device 160 may be configured for applying the fast-transient voltage signal to the measurement electrodes 114. The fast-transient voltage signal may be applied to at least two measurement electrodes 114 in at least one signal application step. The applying the fast-transient voltage signal to the measurement electrodes 114 may comprise applying the fast-transient voltage signal to one of the measurement electrodes 114, in particular to the working electrode 116.

Step ii) further may comprise measuring a first membrane response signal with both the serial resistors $R_3$, $R_4$ as reference and measuring at least one second membrane response signal between the serial resistors $R_3$, $R_4$ with one of the serial resistors $R_3$, $R_4$ as reference. The membrane response signal may be a measured propagation of the applied fast-transient voltage signal. The membrane response signal may be a change of the applied fast-transient voltage signal. The membrane response signal may directly or indirectly refer to equivalent series resistance of the analyte sensor 112. The membrane response signal may be the ohmic and capacitive characterization of the analyte sensor 112 in its in-vivo surroundings. In particular, the membrane response signal does not relate to current response.

In a two-electrode system (FIG. 1), the constant voltage and the fast-transient voltage may be applied to the same or different measurement electrodes 114. In a three-electrode system (FIG. 3), the constant potential difference may be determined and controlled between the working electrode 116 and the reference electrode 120. In order to achieve this, the potentiostat may regulate the voltage between reference electrode 120 and counter electrode 118. Thus, the potential of the working electrode 116 may be determined vs. the reference electrode 120, but the potential of the working electrode 116 may be regulated via the working-electrode-counter-electrode-voltage. The fast-transient voltage signal can be applied between counter electrode 118 and working electrode 116 or between working electrode 116 and reference electrode 120 or counter electrode 118 and reference electrode 120.

The failure detection resistors 124 may be selected suitable for determining a value to be measured such as the electrical resistance of the membrane element 128. The failure detection resistors 124 must reflect the measurement range of the membrane element. The failure detection resistors 124 may reflect required measurement tolerances which must be maintained for correct membrane element resistances.

The fast-transient voltage amplitude may be determined by using the failure detection resistors 124. Before the application of the fast-transient voltage the potentiostat determines the base voltage only. During the application of the fast-transient voltage, the potentiostat 132 determines the sum of the base voltage signal and the fast-transient voltage signal. The potentiostat 132 may be configured for determining the propagation of the fast-transient voltage signal applied to the working electrode 116. The potentiostat 132 may be configured for determining a change or difference $\Delta V_{ex}$ of the measurement voltage signal at the working electrode 116 before application of the fast-transient voltage signal and during the application of the fast-transient voltage signal. The potentiostat 132 may be configured for determining a change or difference $\Delta V_{prop}$ of voltage at the failure detection resistors 124 before application of the fast-transient voltage signal and during the application of the fast-transient voltage signal.

The serial resistors $R_3$, $R_4$ may be arranged as follows. A first one of the serial resistors, e.g., $R_3$, may be connected to the signal generator device 160 and to the other serial resistor, such as $R_4$. The other serial resistor $R_4$ may be connected to the working electrode 115 and thus, to the membrane element 128. As outlined above, step ii) further may comprise measuring a first membrane response signal with both the serial resistors $R_3$, $R_4$ as reference and measuring at least one second membrane response signal between the serial resistors $R_3$, $R_4$ with one of the serial resistors $R_3$, $R_4$ as reference. As outlined above, the fast-transient voltage may be generated by using the signal generator device 160. The continuous analyte monitoring system 110 may comprise a further resistance $R_5$ connected to signal the DAC or PWM 138 configured for preventing that the fast-transient voltage is short-circuit by the output of the DAC or PWM 138. The capacitors C1, C2 and Cd1 may act like short circuits for the rising edge of the pulse. So right after the rising edge of the pulse, an equivalent circuit seeing by the signal generator device 160 can be regarded as made of three resistors in serial, namely $R_3$, $R_4$ and $R_{mem}$. The continuous analyte monitoring system 110, in particular the MCU 134, may comprise at least one second ADC channel (ADC2) 162 arranged between the working electrode 116 and an input of the serial resistor $R_4$. The continuous analyte monitoring system 110, in particular the MCU 134, may comprise at least one third ADC channel (ADC3) 164 arranged between the serial resistors $R_3$ and $R_4$. The continuous analyte monitoring system 110, in particular the MCU 134, may comprise at least one fourth ADC channel (ADC4) 166 arranged between the signal generator device 160 and an input of the serial resistor $R_3$. By measuring the voltage with ADC2 162 and ADC4 166 and thus with both the serial resistors $R_3$, $R_4$ as reference before and after the rising edge of the pulse, it may be possible to calculate the value of a first membrane resistance $R_{mem,1}$, e.g., by $$R_{mem,1} = (R_3 + R_4) \cdot [(ADC2a - ADC2b)/((ADC4a - ADC4b) - (ADC2a - ADC2b))]$$

with ADC2$b$ is the voltage converted by ADC2 before the rising edge of the pulse, ADC2$a$ is the voltage converted by ADC2 after the rising edge of the pulse, ADC4$b$ is the voltage converted by ADC4 before the rising edge of the pulse, ADC4$a$ is the voltage converted by ADC4 after the rising edge of the pulse. By measuring the voltage with ADC3 164 and ADC4 166 and thus with the serial resistors $R_3$ as reference before and after the rising edge of the pulse, it may be possible to calculate the value of $R_{mem} + R_4$, and therefrom a second membrane resistance $R_{mem,2}$, e.g., by $$R_{mem,2} = (R_3 \cdot [(ADC3a - ADC3b)/((ADC4a - ADC4b) - (ADC3a - ADC3b))]) - R_4$$

with ADC3$b$ is the voltage converted by ADC3 before the rising edge of the pulse, ADC3$a$ is the voltage converted by ADC3 after the rising edge of the pulse, ADC4$b$ is the voltage converted by ADC4 before the rising edge of the pulse, ADC4$a$ is the voltage converted by ADC4 after the rising edge of the pulse.

Step iii) may comprise determining the first membrane resistance $R_{mem,1}$ by evaluating of the base voltage and the first membrane response signal and determining the second membrane resistance $R_{mem,2}$ by evaluating of the base voltage and the second membrane response signal. Step iii) may further comprise comparing the first membrane resistance $R_{mem,1}$ and the second membrane resistance $R_{mem,2}$. A failure may be detected if the first membrane resistance $R_{mem,1}$ and the second membrane resistance $R_{mem,2}$ deviate from one another more than the predetermined tolerance. For example, the predetermined tolerance may be ±5%, preferably ±2%. Thus, if both of the values of the membrane resistance are the same within tolerances the membrane element is functional.

With respect to determining the membrane resistance reference is further made to European Patent Application No. 20 162 098.6 filed on Mar. 10, 2020, the content of which is included herein by reference.

The method may comprise detection a failure of other components 122 of the continuous analyte monitoring system 110 such as of the signal generator device 160, the DAC or PWM 138 and/or of at least one ADC channel 140. For example, the DAC or PWM 138 may be tested using ADC2, ADC3 and ADC4 140 channels. If no failure is detected, the electronics is fully functional.

FIG. 3 shows a further embodiment of an equivalent circuit of the continuous analyte monitoring system 110 according to this disclosure for a three-electrode analyte sensor 112. With respect to description of elements of the continuous analyte monitoring system 110 reference is made to the description of FIG. 1 with the difference that in FIG. 3 a third electrode, the reference electrode 130 is used. A further amplifier (Amp2) 168 is connected to the reference electrode 120. Instead of putting on the working electrode 116 to 50 mVolts more than the potential of the counter electrode 118, in FIG. 3, the working electrode 116 is put 50 mVolts more than the voltage of the reference electrode 120. Moreover, the continuous analyte monitoring system 110 comprises a further output O2 170 which may be normally put in three states. Thus, this line is floating, like if it was not connected to anything. As no current is flowing into R6 and R7, Amp2 is a voltage follower, this means that the output has the same voltage as the minus input.

The detecting the failure of the components 122 of the continuous analyte monitoring system 110 may be exactly the same as for a two-electrode sensor 112. For the three-electrode system, however, there may be need for also testing the amplifier Amp2 168. A failure of Amp2 168 would result in applying a wrong polarization voltage on the analyte sensor 112 and the current, and thus the analyte detection, would be incorrect. To test Amp2 168, the output O2 170 may be put to ground. Amp2 168 may in this situation function as a voltage amplifier and no more a voltage follower. The amplification factor may be 1+R6/R7. For example, R7 may be 56 kΩ and R6 may be 5.6 kΩ. The amplifier 168 may be connected to a fifth ADC channel (ADC5) 172. For example, the ADC5 172 may measure 300 mV when O2 170 is in three states and the amplifier Amp2 168 is just a voltage follower. When O2 170 is put at ground, the amplifier Amp2 168 is becoming an amplifier with a factor of 1.1. So if ADC5 172 is measuring 330 mV when O2 170 is put at ground, this would imply that the amplifier Amp2 is correctly working.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 continuous analyte monitoring system,
112 analyte sensor
114 measurement electrodes
116 working electrode
118 counter electrode
120 reference electrode
122 Component
124 failure detection resistor
126 measurement resistance
128 membrane element
130 controlling unit
132 Potentiostat

134 microcontroller unit
136 sensor contacts
138 Digital to Analog converter (DAC) or at least one Pulse Width Modulator (PWM)
140 Analog to Digital channel
142 first ADC channel
144 first measurement resistance
146 Amplifier
148 output O1
150 second measurement resistance
152 Step i)
154 Step ii)
156 Step iii)
158 analyte measurement step
160 signal generator device
162 second ADC channel
164 third ADC channel
166 fourth ADC channel
168 amplifier Amp2
170 output O2
172 fifth ADC channel

What is claimed is:

1. A method for detecting a failure of a measurement resistor of a continuous analyte monitoring system, wherein the continuous analyte monitoring system has a failure detection resistor $R_2$ and an analyte sensor comprising at least two measurement electrodes, the method comprising:
    i) applying a constant voltage between the at least two measurement electrodes and measuring a first response signal, the first response signal being a first current $I_1$ measured at a first measurement resistor $R_1$;
    ii) applying to the continuous monitoring system a second current $I_2$ as a failure detection signal distinguishable from the constant voltage and/or from the first response signal in frequency and/or in height;
    iii) measuring a second response signal, $I_{tot}$, to the failure detection signal using the failure detection resistor $R_2$, wherein $I_{tot}$ is the current at $R_2$ after application of the constant voltage and $I_2$;
    iv) comparing the difference between the sum $(I_{1+I2})$ and $I_{tot}$, wherein a failure is detected if the difference between $(I_1+I_2)$ and $I_{tot}$ deviates from an expected value by more than a predetermined tolerance.

2. The method according to claim 1, wherein the second current $I_2$ is around 5 nA or less.

3. The method according to claim 1, wherein the constant voltage is about 50 mV.

4. The method according to claim 1, wherein the analyte sensor is a two-electrode sensor comprising two measurement electrodes or a three-electrode sensor comprising three measurement electrodes.

5. The method according to claim 1, wherein the analyte sensor is an in vivo sensor.

6. The method according to claim 1, wherein the method is performed in vivo.

7. The method according to claim 1, wherein the method further comprises at least one analyte measurement step during which the concentration of at least one analyte is determined.

8. A continuous analyte monitoring system for determining a concentration of at least one analyte in body fluid, the system comprising:
    an analyte sensor having at least two measurement electrodes;
    a measurement resistor and at least one failure detection resistor $R_2$; and
    a controller configured for performing steps i)-iv) of claim 1.

9. A method for detecting a failure of a membrane of an analyte sensor of a continuous analyte monitoring system, wherein the continuous analyte monitoring system has two failure detection resistors $R_3$ and $R_4$ in series with a resistance of the membrane, and the analyte sensor has at least two measurement electrodes, the method comprising:
    i) applying a constant voltage between the at least two measurement electrodes and measuring a first response signal, the first response signal being a base voltage of the continuous analyte monitoring system;
    ii) applying to the measurement electrodes a fast transient voltage as a failure detection signal distinguishable from the constant voltage and/or from the first response signal in frequency and/or in height;
    iii) measuring a first membrane response signal with both resistors $R_3$ and $R_4$ being a reference and measuring a second membrane response signal between resistors $R_3$ and $R_4$ with one of the resistors $R_3$ and $R_4$ being a reference;
    iv) determining a first membrane resistance $R_{mem,1}$ by evaluating the base voltage and the first membrane response signal and determining a second membrane resistance $R_{mem,2}$ by evaluating the base voltage and the second membrane response signal, wherein a failure is detected if $R_{mem,1}$ and $R_{mem,2}$ deviate from one another by more than a predetermined tolerance.

10. The method according to claim 9, wherein the fast-transient voltage signal has a square wave form or a sine wave signal form.

11. The method according to claim 9, wherein the fast-transient voltage signal comprises a pulse, wherein a pulse duration is selected from the group consisting of $\leq 20$ μs and $\leq 10$ μs.

* * * * *